US007645452B2

(12) United States Patent
Thompson et al.

(10) Patent No.: US 7,645,452 B2
(45) Date of Patent: Jan. 12, 2010

(54) RTVP BASED COMPOSITIONS AND METHODS FOR THE TREATMENT OF PROSTATE CANCER

(75) Inventors: Timothy C. Thompson, Houston, TX (US); Chengzhen Ren, Pearland, TX (US)

(73) Assignee: Baylor College of Medicine, Houston, TX (US)

( * ) Notice: Subject to any disclaimer, the term of this patent is extended or adjusted under 35 U.S.C. 154(b) by 339 days.

(21) Appl. No.: 10/417,727

(22) Filed: Apr. 17, 2003

(65) Prior Publication Data

US 2004/0009508 A1 Jan. 15, 2004

Related U.S. Application Data

(62) Division of application No. 09/876,225, filed on Jun. 8, 2001, now abandoned.

(60) Provisional application No. 60/209,989, filed on Jun. 8, 2000.

(51) Int. Cl.
*A61K 39/00* (2006.01)

(52) U.S. Cl. ......................... 424/184.1; 514/2; 530/350

(58) Field of Classification Search ..................... 514/2; 424/9.2, 184.1, 185.1; 530/300, 350
See application file for complete search history.

(56) References Cited

U.S. PATENT DOCUMENTS

| | | | | |
|---|---|---|---|---|
| 5,789,200 | A * | 8/1998 | Kola et al. | 435/69.1 |
| 6,071,874 | A | 6/2000 | Bandman et al. | |
| 6,335,170 | B1 | 1/2002 | Orntoft et al. | |
| 6,783,969 | B1 | 8/2004 | Tang et al. | |
| 2002/0052025 | A1 | 5/2002 | Thompson et al. | |
| 2002/0052308 | A1 | 5/2002 | Rosen et al. | |
| 2003/0119009 | A1 | 6/2003 | Stuart et al. | |
| 2003/0144494 | A1 | 7/2003 | Algate et al. | |
| 2003/0219743 | A1 | 11/2003 | Tang et al. | |
| 2003/0236392 | A1 | 12/2003 | Isogai et al. | |
| 2004/0009508 | A1 | 1/2004 | Thompson et al. | |
| 2004/0029151 | A1 | 2/2004 | Mahadevappa et al. | |

FOREIGN PATENT DOCUMENTS

| | | |
|---|---|---|
| WO | WO98/29448 | 7/1998 |
| WO | WO 2004/111200 | 12/2004 |
| WO | WO 2005/002413 | 1/2005 |

OTHER PUBLICATIONS

Bowie et al (Science, 1990, 257:1306-1310).*
Burgess et al ( J of Cell Bio. 111:2129-2138, 1990).*
Lazar et al (Molecular and Cellular Biology, 1988, 8:1247-1252).*
Stedman's medical dictionary, 25th ed, 1990, p. 1029-1030.*
WO200055350-A1 , and MPSRCH search report, 2006, us-10-417-727-3.rag, pp. 6-7.*
Rich et al, 1996 (Gene, 180: 125-130) and MPSRCH search report, 2006, us-10-417-727-3.rpr, p. 1.*
Kimmel et al, 1987 (J. Neurosurg, 66:161-171).*
Kirkin et al, 1998 (APMIS, 106 : 665-679).*
Boon, 1992 (Adv Can Res, 58:177-210).*
Ezzell, 1995 (J. NIH Res, 7:46-49).*
Gura, 1997, (Science, 278:1041-1042).*
Jain, 1994 (Sci. Am., 271:58-65).*
Curti, 1993 (Crit. Rev. in Oncology/Hematology, 14:29-39).*
Hartwell et al (Science, 1997, 278:1064-1068).*
Zips et al, 2005, In vivo, 19: 1-8.*
Lee et al, 1999, J Immunol, 163: 6292-6300.*
Dermer, 1994 (Bio/Technology, 12:320).*
Drexler et al, 1993 (Leukemia and Lymphoma, 9:1-25).*
Tian, J et al, 2004 (Physiol Genomics, 17: 170-182).*
Van Dyke D L et al, 2003 (Cancer Genetics and Cytogenetics 241: 137-141).*
Kunkel, P, et al, 2001 (Neuro-oncology 3(2): 82-88).*
El-Deiry, W.S.; "Regulation of p53 downstream genes" Semin Cancer Biol 8,345-57 (1998).
Giaccia, A.J. & Kastan, M.B.;"The complexity of p53 modulation: emerging patterns from divergent signals" Genes Dev 12, 2973-83 (1998).
Burns, T.F. & El-Diery, W.S.;"The p53 pathway and apoptosis" J Cell Physiol 181, 231-9 (1999).
Vogelstein, B. & Kinzler, K.W.;"p53 function and dysfunction" Cell 70, 523-6 (1992).
Thompson, T.C., et al.; "Oncogenes, growth factors, and hormones in prostate cancer" Hormones and growth factors in development and neoplasia (eds. Dickson, R.B. & Salomon, D.S.) 327-359 (Wiley-Liss, New York, 1998).

(Continued)

*Primary Examiner*—Larry R. Helms
*Assistant Examiner*—Minh-Tam Davis
(74) *Attorney, Agent, or Firm*—Vinson & Elkins LLP

(57) ABSTRACT

This invention relates to a gene encoding RTVP that has been shown to be up-regulated by p53 using differential display-PCR and subsequently by co-transfection studies. RTVP-1 mRNA is abundant in normal mouse and human prostatic epithelial cells and primary tumors, but is significantly down regulated in metastatic mouse and human prostate cancer. In prostate cancer cells overexpression of the mouse RTVP-1 gene (mRTVP-1) induced apoptosis that was accompanied by increased caspase 8, 9 and 3 activities. mRTVP-1-stimulated apoptosis was also associated with increased levels of bax, bad and activated BID; reduced levels of bcl-2 and bcl-$X_L$; and cytosolic cytochrome c accumulation. Adenoviral-vector-mediated mRTVP-1 expression lead to potent growth suppression and antimetastatic activities in an orthotopic mouse model of prostate cancer in vivo. These therapeutic activities were associated with anti-angiogenic effects and importantly a local and systemic immune response. Accordingly, p53 was linked with suppression of metastasis through its induction of mRTVP-1, which can concurrently induce apoptosis, suppress angiogenesis and stimulate an antitumor immune response. Thus, the invention includes compositions and methods, based on RTVP nucleic acid, polypeptides, and antibodies, for use in the treatment, prevention and detection of neoplastic disease and, specifically, metastatic prostatic neoplasia.

4 Claims, 35 Drawing Sheets

OTHER PUBLICATIONS

Thompson, T.C., et al.; "Loss of p53 function leads to metastasis in *ras+myc*-initiated mouse prostate cancer," Oncogene, 1995, vol. 10, pp. 869-879.

Navone, N.M. et al.; "p53 protein accumulation and gene mutation in the progression of human prostate carcinoma" J Natl Cancer Inst 85, 1657-69 (1993).

Eastham, J.A. et al.; "Association of p53 mutations with metastatic prostate cancer" Clin Cancer Res 1, 1111-8 (1995).

Mirchandani, D. et al.; "Heterogeneity in intratumor distribution of p53 mutations in human prostate cancer" Am J Pathol 147, 92-101 (1995).

Yang, G. et al.; "Clustered p53 immunostaining: a novel pattern associated with prostate cancer progression" Clin Cancer Res 2, 399-401 (1996).

Stapleton, A.M. et al.; "Primary human prostate cancer cells harboring p53 mutations are clonally expanded in metastases" Clin Cancer Res 3, 1389-97 (1997).

Quinn, D.I. et al.; "Prognostic significance of p53 nuclear accumulation in localized prostate cancer treated with radical prostatectomy" Cancer Res 60, 1585-94 (2000).

Stapleton, A.M. et al.; "Assessment of the biologic markers p53, Ki-67, and apoptotic index as predictive indicators of prostate carcinoma recurrence after surgery" Cancer 82, 168-75 (1998).

Miyashita, T. & Reed, J.C.; "Tumor suppressor p53 is a direct transcriptional activator of the human bax gene" Cell 80, 293-9 (1995).

Sheikh, M.S. et al.; "p53-dependent and -independent regulation of the death receptor KILLER/DR5 gene expression in response to genotoxic stress and tumor necrosis factor alpha" Cancer Res 58, 1593-8 (1998).

Oda, K. et al.; "p53AIP1, a potential mediator of p53-dependent apoptosis, and its regulation by Ser-46-phosphorylated p53" Cell 102, 849-62 (2000).

Zhu, J. & Chen, X.; "MCG10, a novel p53 target gene that encodes a KH domain RNA-binding protein, is capable of inducing apoptosis and cell cycle arrest in G(2)-M" Mol Cell Biol 20, 5602-18 (2000).

Dameron, K.M., et al.; "Control of angiogenesis in fibroblasts by p53 regulation of thrombospondin-1" Science 265, 1582-4 (1994).

Lopez-Ocejo, O. et al.; "Oncogenes and tumor angiogenesis: the HPC-16 E6 oncoprotein activates the vascular endothetial growth factor (VEGF) gene promotor in a p53 independent manner" Oncogene 19, 4611-20 (2000).

Zou, Z. et al.; "p53 regulates the expression of the tumor suppressor gene maspin" J Biol Chem 275, 605 1-4 (2000).

Zhang, M., et al.; "Maspin is an angiogenesis inhibitor" Nat Med 6, 196-9 (2000).

Zhang, Y., et al.; "Cell cycle inhibition by the anti-angiogenic agent TNP-470 is mediated by p53 and p21WAF1/CIP1" Proc Natl Acad Sci USA 97, 6427-32 (2000).

Murphy, E.V., et al.; "The human glioma pathogenesis-related protein is structurally related to plant pathogenesis-related protein and its gene is expressed specifically in brain tumors" Gene 159, 131-5 (1995).

Rich, T., et al.; "RTVP-1, a novel human gene with sequence similarity to genes of diverse species, is expressed in tumor cell lines of glial but not neuronal origin" Gene 180, 125-30 (1996).

Gingras, M.C. & Margolin, J.F.; "Differential expression of multiple unexpected genes during U937 cell and macrophage differentiation detected by suppressive subtractive hybridization" Exp Hematol 28, 65-76 (2000).

Cho, Y. et al.; "Crystal structure of a p53 tumor suppressor-DNA complex: understanding tumorigenic mutations" Science 265, 346-55 (1994).

Tokino, T. et al.; "p53 tagged sites from human genomic DNA" Hum Mol Genet 3, 1537-42 (1994).

Yu, J. et al.; "Identification and classification of p53-regulated genes" Proc Natl Acad Sci USA 96, 14517-22 (1999).

Shiraishi, K. et al..; "Identification of fractalkine, a CX3C-type chemokine, as a direct target of p35" Cancer Res 60, 3722-6 (2000).

Bazan, J.F. et al.; "A new class of membrane-bound chemokine with a CX3C motif" Nature 385, 640-4 (1997).

Pan, Y. et al.; "Neurotactin, a membrane-anchored chemokine upregulated in brain inflammation" Nature 387, 611-7 (1997).

Sakr, W.A. et al.; "Allelic loss in locally metastatic, multisampled prostate cancer" Cancer Res 54, 3273-7 (1994).

Qian, J. et al.; "Chromosomal anomalies in prostatic intraepithelial neoplasia and carcinoma detected by fluorescence in situ hybridization" Cancer Res 55, 5408-14 (1995).

Ren, C., et al.; "Reduced lysyl oxidase messenger RNA levels in experimental and human prostate cancer" Cancer Res 58, 1285-90 (1998).

Yang, G. et al.; "Elevated expression of caveolin is associated with prostate and breast cancer" Clin Cancer Res 4, 1873-80 (1998).

Nasu, Y. et al.; "Suppression of caveolin expression induces androgen sensitivity in metastatic androgen-insensitive mouse prostate cancer cells" Nat Med 4, 1062-4 (1998).

Baker, S.J., et al.; "Suppression of human colorectal carcinoma cell growth by wild-type p53" Science 249, 912-5 (1990).

Timme, T.L. et al.; "Caveolin-1 is regulated by c-myc and suppresses c-myc-induced apoptosis" Oncogene 19, 3256-65 (2000).

Patel, S.D. et al.; "The p53-Independent tumoricidal activity of an adenoviral vector encoding a p27-p16 fusion tumor suppressor gene" Mol Ther 2, 161-9 (2000).

Hall, S.J. et al.; "Cooperative therapeutic effects of androgen ablation and adenovirus-mediated herpes simplex virus thymidine kinase gene and ganciclovir therapy in experimental prostate cancer" Cancer Gene Ther 6, 54-63 (1999).

Nasu, Y. et al.; "Adenovirus-mediated interleukin-12 gene therapy for prostate cancer: suppression of orthotopic tumor growth and pre-established lung metastases in an orthotopic model" Gene Ther 6, 338-49 (1999).

Eastham, J.A. et al; "In vivo gene therapy with p53 or p21 adenovirus for prostate cancer" Cancer Res 55, 5151-5 (1995).

Baley, P.A., et al.; "Progression to androgen insensitivity in a novel in vitro mouse model for prostate cancer" J Steroid Biochem Mol Biol 52, 403-13 (1995).

Osoegawa, K. et al.; "Bacterial artificial chromosome libraries for mouse sequencing and functional analysis" Genome Res 10, 116-28 (2000).

"Mus musculus early blastocyst cDNA, clone 01B00051IC04"; Database EMBL 'Online!'; Database accession No. C88861, XP002212367; May 28, 1998.

"vz40g06.r1 Soares 2NbMT Mus musculus cDNA clone . . . similar to Glioma Pathogenesis-Related Protein"; Database EMBL 'Online!'; Database accession No. AA929313, XP002212368; Apr. 27, 1998.

"vf97h09.y1 Soares mouse mammary gland cDNA clone . . . similar to Glioma Pathogenesis-Related Protein"; Database EMBL 'Online!'; Database accession No. AI614880; XP002212369; Apr. 26, 1999.

"Mus Musculus ES cells cDNA, Riken full-length enriched library, clone: 2410114014: homolog to Glioma Pathogenesis—related protein (RTVP-1 Protein)"; Database Accession No. AK010768; XP-002212370; Feb. 8, 2001.

"*H. sapiens* mRNA for RTVP-1 protein," Database Genbank 'Online!'; Database accession No. X91911.

"*Homo sapiens* glioma pathogenesis-related protein (GliPR) mRNA, complete cds." Database Genbank 'Online!'; Database accession No. U16307.

"Mus musculus ES cells cDNA, Riken Full-Length Enriched Library, Clone 2410114014 product: weakly similar to glioma" Database EMBL 'Online!' EBI; Database accession No. AK010768, XP0102212370.

Burgess Wilson H., et al.; "Possible dissociation of the heparin-binding and mitogenic activities of heparin-binding (acidic fibroblast) growth factor-1 from its receptor-binding activities by site-directed mutagenesis of a single lysine residue," Journal of Cell Biology, Nov. 1990, 111: 2129-2138.

Lazar, Eliane, et al.; "Transforming growth factor alpha: mutation of aspartic acid 47 and leucine 48 results in different biological activities," Molecular and Cell Biology, 1988, 8: 1247-1252.

Tao, Mi-Hua, et al., "Studies of aglycosylated chimeric mouse-human IgG; Role of carbohydrate in the structure and effector functions mediated by the human IgG constant region," The Journal of Immunology, Oct. 15, 1989, 143 (8),: 2595-2601.
Gillies, Stephen, et al.; "Antigen binding and biological activities of engineered mutant chimeric antibodies with human tumor specificities," Human Antibodies and Hybridomas, 1990, vol. 1 (No. 1): 47-54.
Gura, Trisha, "Systems for identifying new drugs are often faulty," Science, Nov. 7, 1997, vol. 278: 1041-1042.
Jain, Rakesh K., "Barriers to drug delivery in solid tumors," Scientific American, Jul. 1994, 271:58-65.
Curti, Brendan D., "Physical barriers to drug delivery in tumors," Crit. Rev. in Oncology/Hematology, 1993, 14:29-39.
Hartwell, et al. "Integrating genetic approaches into the discovery of anticancer drugs," Science, vol. 278, Nov. 7, 1997:1064-1068.
Herbert et al.; The Dictionary of Immunology, Academic Press, 4th edition, 1995, p. 58.
Greenspan, et al.; "Defining epitopes: It's not as easy as it seems," Nature Biotechnology, vol. 17: 936-937 (Oct. 1999).
Jansen, M, et al.; "Translational control of gene expression," Pediatric Res, 1995, 37 (6): 681-686.
Alberts, et al.; Molecular Biology of the Cell, 3rd edition, 1994, p. 465.
Shantz and Pegg., "Translational regulation of omithine decarboxylase and other enzymes of the polyamine pathway," Int J of Biochem and Cell Biol., 1999, vol. 31, pp. 107-122.
McClean and Hill, "Evidence of post-translational regulation of P-Glycoprotein associated with the expression of a distinctive multiple drug-resistant phenotype in Chinese hamster ovary cells," Eur J of Cancer, 1993, vol. 29A, pp. 2243-2248.
Fu, et al.; "Translational regulation of human p53 gene expression," EMBO Journal, 1996, vol. 15, pp. 4392-4401.
Yokota, J., et al.; "Altered expression of the retinoblastoma (RB) gene in small-cell carcinoma of the lung," Oncogene, 1988, vol. 3, pp. 471-475.
Thompson, T.C., et al.; "Caveolin-1, a metastasis-related gene that promotes cell survival in prostate cancer," Apoptosis, 1999, vol. 4, No. 4, pp. 233-237.
Magelsdorf, David J. et al.; "Characterization of three genes that mediate the action of 9-*cis* retinoic acid," Genes & Development, 1992, vol. 6, pp. 329-344.
Anderson, W. French; "Human gene therapy," Nature, Apr. 30, 1998, vol. 392, pp. 25-30.
Thompson, Timothy C., et al.; "Multistage Carcinogenesis Induced by *ras* and *myc* Oncogenes in a Reconstituted Organ," Cell, Mar. 24, 1989, vol. 56, pp. 917-930.
Thompson, Timothy C., et al.; "Transforming Growth Factor β1 as a Biomarker for Prostate Cancer," Journal of Cellular Biochemistry, 1992, Supplement 16H, pp. 54-61.
Thompson, Timothy C., et al.; "Genetic Predisposition and Mesenchymal-Epithelial Interactions in *ras+myc*-Induced Carcinogenesis in Reconstituted Mouse Prostate," Molecular Carcinogenesis, 1993, vol. 7, pp. 165-179.
Sargiacomo, Massimo, et al.; "Oligomeric structure of caveolin: Implications for caveolae membrane organization," Cell Biology, Sep. 1995, vol. 92, pp. 9407-9411.
Tulchinsky, E., et al.; "Transcriptional analysis of the *mts1* gene with specific reference to 5' flanking sequences," Biochemistry, Oct. 1992, vol. 89, pp. 9146-9150.
Eastham, James A., et al.; "Prostate Cancer Gene Therapy: Herpes Simplex Virus Thymidine Kinase Gene Transduction Followed by Ganciclovir in Mouse and Human Prostate Cancer Models," Human Gene Therapy, Mar. 1, 1996, vol. 7, pp. 515-523.
Fielding, Christopher J., et al.; "Caveolin mRNA levels are up-regulated by free cholesterol and down-regulated by oxysterols in fibroblast monolayers," Cell Biology, Apr. 1997, vol. 94, pp. 3753-3758.
Bist, Anita, et al.; "Two sterol regulatory element-like sequences mediate up-regulation of caveolin gene transcription in response to low density lipoprotein free cholesterol," Cell Biology, Sep. 1997, vol. 94, pp. 10693-10698.
Thompson, Timothy C.; "Metastasis-related genes in prostate cancer: The role of caveolin-1," Cancer and Metastasis Reviews, 1999, vol. 17, pp. 439-442.
Wood, Jr., David P., et al.; "Sensitivity of Immunohistochemistry and Polymerase Chain Reaction in Detecting Prostate Cancer Cells in Bone Marrow," The Journal of Histochemistry and Cytochemistry, 1994, vol. 42, No. 4, pp. 505-511.
Song, Kenneth S., et al.; "Expression of Caveolin-3 in Skeletal, Cardiac, and Smooth Muscle Cells," The Journal of Biological Chemistry, 1996, vol. 271, No. 25, pp. 15160-15165.
Helothermine precursor (HLTx); Database accession No. Q91055, Nov. 1, 1997.
Sperm-coating glycoprotein 1 precursor (SCP 1) (Acidic epididymal glycoprotein 1) (Cysteine-rich secretory protein-1) (Crisp-1); Database accession No. Q03401, Oct. 1, 1993.
"Testis-specific protein TPX-1 precursor"; Database accession No. P16563, Aug. 1, 1990.
Sperm-coating glycoprotein precursor (SCP) (Acidic epididymal glycoprotein) (Protein D) (Protein E) (Protein IV) (Sialoprotein) (32kDa epididymal protein); Database accession No. P12020, Oct. 1, 1989.
Boggs, Will, MD; "Research shows tumor-suppressing protein action"; Gene Therapy News, Jun. 7.
University of California, Berkely; "Researchers find first prostate cancer antigen, providing hope for an eventual vaccine against the tumor"; Science Daily Magazine, Apr. 9, 2001.
European Search Report for corresponding App. 01944345.6 in Europe, Aug. 7, 2005, Baylor College of Med.

* cited by examiner

TGGAGCTCAGAGGCAGAGCACTTGTCTAGCATAAACAACCCTGGGTTAA
TCCGAGCTCCAACAGGGAAACAGTCTGCAGACTGAGAGAACCGAGCATTC
TATCAGAACCCCGCAGCTCTGGATTCTAGGTCCAGCAGCAACCAGAGAGA
CCATGCAGGTCATCCTTGCTGTGATAGTCTGGATGGCTTCGTCTGTGTCT
AGTTCTTCATTTACAGCAAGCACTTTGCCAGATATAACAAACGAGGACTT
CATTAAAGAATGTGTTCAAGTTCACAACCAGCTTCGGTCAAAAGTGAGTC
CACCAGCCCGGAATATGCTGTACATGTCTTGGGACCCAAAACTAGCCCAA
ATTGCAAAAGCATGGACAAAATCTTGTGAATTTAAACACAACCCACAGCT
GCATTCACGGATACACCCAAATTTCACCGCCCTGGGAGAGAATATCTGGC
TTGGCTCTCTATCCATCTTTTCAGTATCCTCAGCCATCTCTGCCTGGTATGA
AGAAATTAAGCACTATGACTTCAGCACTAGGAAATGTAGACATGTCTGTG
GCCATTATACTCAGGTTGTTTGGGCAGACAGTTACAAACTTGGCTGTGCA
GTGCAACTTTGCCCTAATGGAGCAAATTTTATATGCGACTATGGACCAGC
AGGAAATTACCCAACGTGGCCATATAAGCAAGGAGCCACGTGCAGTGATT
GCCCAAAAGATGACAAGTGTCTCAACAGTCTCTGATTAACCCACGACGA
GACCAGGTCTCACGTTACTACTCTGTCGCATTATCCAGACTGGCCTATATA
CCTGCGTAACAGATACACATCTCTCTTTCTCATTGCTAAGTCGGTTCT
CCTATTACTGTCTGTTATAATTACCATCTGGGTAAAGCACAAATATCCTA
ACTTGGTTCTTTTGGACTAAAGCTGTGGTTGGGGGACAACTGAATCAC
ATGCGGCTATTTAAAAACTTTTCAATAAAATCTCAGTCAAAAGAAAAAAA
AAAAAAAAAAA (SEQ ID NO:1)

FIG. 1A

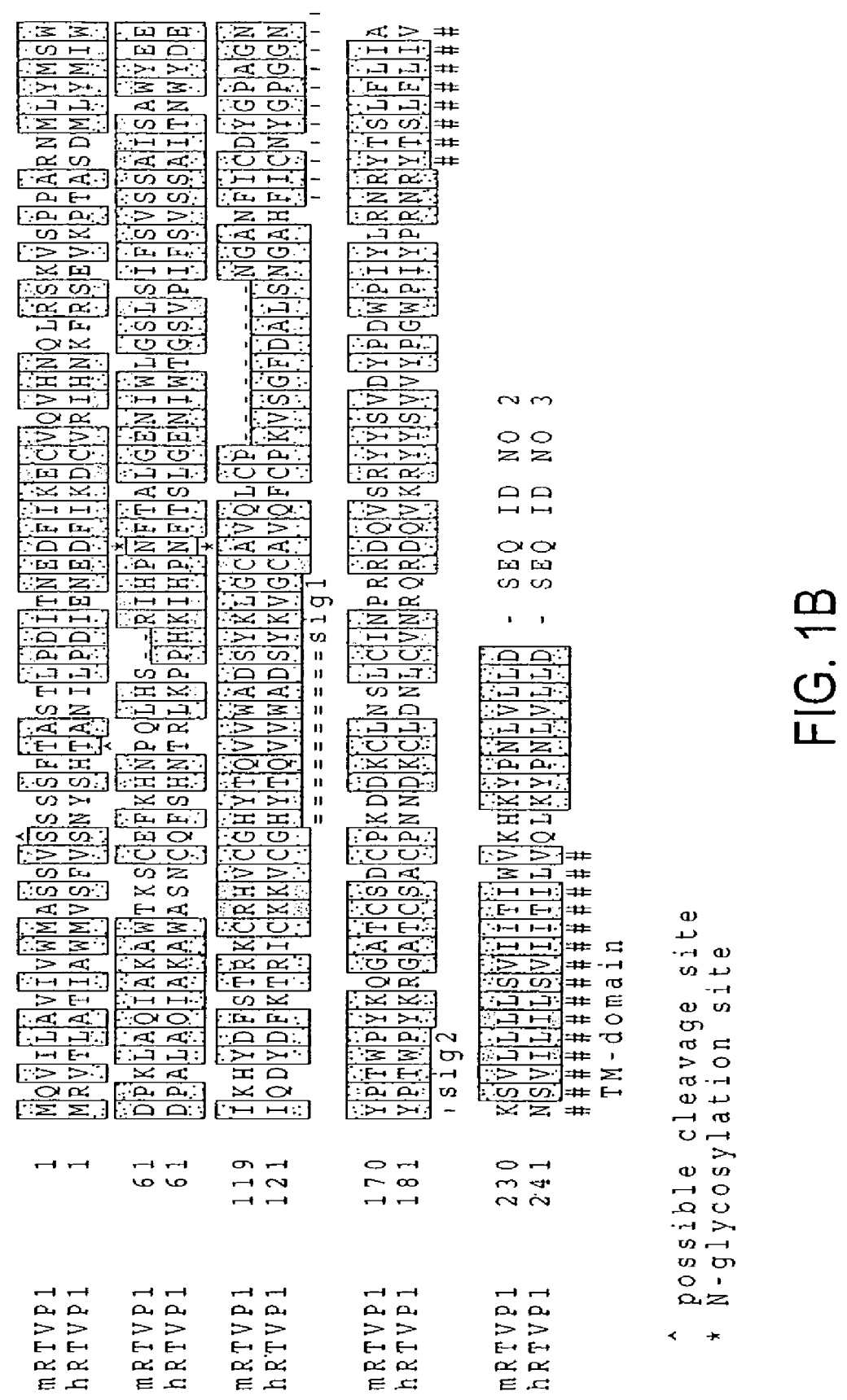

```
mRTVP1    1  MQVILAVIVWMASSVSSSSFTASTLPDITNEDFIKECVQVHNQLRSKVSPPARNMLYMSW
hRTVP1    1  MRVTLATIAWMVSFVSNYSHTANILPDIENEDFIKDCVRIHNKFRSEVKPTASDMLYMIW

mRTVP1   61  DPKLAQIAKAWTKSCEFKHNPQLHS--RIHPNFTALGENIWLGSLSIFSVSSAISAWYEE
hRTVP1   61  DPALAQIAKAWASNCQFSHNTRLKPPHKIHPNFTSLGENIWTGSVPIFSVSSAITNWYDE

mRTVP1  119  IKHYDFSTRKCRHVCGHYTQVVWADSYKLGCAVQLCP---------NGANFICDYGPAGN
hRTVP1  121  IQDYDFKTRICKKVCGHYTQVVWADSYKVGCAVQFCPKVSGFDALSNGAHFICNYGPGGN
                            ==========sig1

mRTVP1  170  YPTWPYKQGATCSDCPKDDKCLNSLCINPRRDQVSRYYSVDYPDWPIYLRNRYTSLFLIA
hRTVP1  181  YPTWPYKRGATCSACPNNDKCLDNLCVNRQRDQVKRYYSVVYPGWPIYPRNRYTSLFLIV
             sig2                                                ########

mRTVP1  230  KSVLLLLSVIITIWVKHKYPNLVLLD  - SEQ ID NO 2
hRTVP1  241  NSVILILSVIITILVQLKYPNLVLLD  - SEQ ID NO 3
             ##############
              TM-domain
```

^ possible cleavage site
* N-glycosylation site

FIG. 1B

MOUSE

NI-As

HUMAN

NI-As

MOUSE

PCa-As

HUMAN

PCa-As

PCaMet-As

MOUSE

PCaMet-As

HUMAN

PCa-S

MOUSE

PCa-S

HUMAN

AdβGal

PFU/RING 5 X $10^7$

AdmRTVP-1

PFU/RING 5 X $10^7$

AdβGal

PFU/RING 1 X $10^8$

AdmRTVP-1

PFU/RING 1 X $10^8$

AdβGal

PFU/RING 5 X $10^8$

AdmRTVP-1

PFU/RING 5 X $10^8$

- % OF CELLS KILLED EXCEEDS NUMBER OF CELLS TRANSDUCED BY VIRUS
- OBSERVED *IN VIVO*
- PROPOSED MECHANISMS:
  - SECRETION/RELEASE OF GROWTH INHIBITORY FACTORS
  - ANTI-ANGIOGENIC EFFECTS:
    - ↓ VEGF
    - ↑ INHIBITORS (E.G. TSB1)
  - SECRETION OF CHEMOKINES → IMMUNE INFILTRATION

FIG. 7B

HUMAN TISSUES

HEART
BRAIN
PLACENTA
LUNG
LIVER
SKEL. MUSCLE
KIDNEY
PANCREAS
SPLEEN
THYMUS
PROSTATE
TESTIS
OVARY
SM. INTESTINE
COLON
P BLOOD LYMPHOCYTE

RTVP-1

MOUSE TISSUES

KIDNEY p53 -/-
AP p53 -/-
DLP p53 -/-
VP p53 -/-
ANTERIOR PROSTATE
DORSOLATERAL PROSTATE
VENTRAL PROSTATE
SEMINAL VESICLE
TESTIS
KIDNEY
BLADDER
LUNG
HEART
BRAIN
COLON
LIVER
SPLEEN
MUSCLE

RTVP-1

RTVP-1 -
PROSTATE CANCER

RTVP-1 +
PROSTATE CANCER

RTVP BASED COMPOSITIONS AND METHODS FOR THE TREATMENT OF PROSTATE CANCER

REFERENCE TO RELATED APPLICATIONS

This patent application is a divisional of United States Patent Application, entitled RTVP Based Compositions and Methods for the Treatment of Prostate Cancer, Ser. No. 09/876,225, filed Jun. 8, 2001, now abandoned, which is a continuation of United States Provisional Patent Application, entitled p-53 Regulated Gene Encoding p144-3 and p144-3 Protein, Ser. No. 60/209,989, filed Jun. 8, 2000.

RIGHTS IN THE INVENTION

This invention was made, in part, with United States government support under grant number ROI-50588, awarded by the National Cancer Institute, and also grant number P50-58204, awarded by the National Cancer Institute, Specialized Program or Research Excellence (SPORE), and the United States Government has certain rights in the invention.

BACKGROUND OF THE INVENTION

1. Field of the Invention

The present invention relates to RTVP genes and associated sequences, to RTVP proteins, and to methods and tools using these sequences for the diagnosis, study and treatment of disease. Further, the invention includes RTVP receptor protein and the gene which encodes this protein. In particular, the invention relates to compositions and methods based on RTVP for the treatment, prevention and detection of prostatic neoplasia such as prostate carcinoma and associated metastatic disease.

2. Description of the Background

The prostate is a walnut size gland that is part of the male reproductive system that makes and stores seminal fluid. It is located below the bladder, in front of the rectum, and surrounds the upper part of the urethra. To work properly, the prostate needs male hormones (androgens). The main male hormone is testosterone, which is produced by the testicles. Prostate cancer or PC is characterized by the uncontrolled growth of prostate epithelial cells to form one or more tumors. Localized PC is treated very successfully and results in a 100% five-year survival rate. Metastatic PC has a 31% survival rate, about 80% of which attacks the bone with a significant portion of the remainder attacking the lungs. PC that metastasizes to the bone is not bone cancer and is treated as later stage or distant PC.

The American Cancer Society reports that excluding skin cancer, PC is the most common malignancy and the second leading cause of cancer death among men in the US. The incidence and mortality of PC increase with age, 77% of men with new diagnoses of prostate cancer each year are over the age of 65. PC is rare in younger men, with an incidence rate of less than one case per 100,000 for men under age 40. However, the rate climbs to 82 per 100,000 for men ages 50-54, 518 for ages 60-64, and 1,326 for ages 70-74. African-Americans are twice as likely to develop and die from PC than men of other ethnic and racial groups.

The number of PC cases will increase dramatically during the next four decades as the demographics of the Baby Boom generation take effect and the reduction of deaths from cardiovascular and smoking-related diseases increase the size of the 60-84 year old population segment. It is estimated that approximately 570,000 new cases of PC will be diagnosed in 2030 (when there will be close to 50 million men in this population group), and estimated over 2,000,000 men in treatment. This compares to an incidence of 168,665 new cases in 1995.

Surgery and/or radiotherapy remain the treatments of choice for early PC. Typically, surgery requires complete removal of the prostate (radical prostatectomy), and quite often removal of surrounding lymph nodes (lymphadenectomy). Radiotherapy, which is also used as adjuvant therapy, may be either external or interstitial and involves exposure of the effected tissue to radioisotopes such as $^{125}I$. With more advanced forms of PC, endocrine therapy is often the preferred treatment. The aim of this therapy is to deprive prostate cells, and presumably transformed prostate cells as well, of testosterone. This can be accomplished by orchiectomy (castration), or administration of drugs (e.g. leuprolide, goserelin), antiandrogens (e.g. flutamide and bicalutamide), estrogens or synthetic hormones that are agonists of luteinizing hormone-releasing hormone, which directly inhibit testicular and organ synthesis and suppress luteinizing hormone secretion which in turn leads to reduced testosterone secretion by the testes. Despite the advances made in achieving a pharmacologic orchiectomy, the survival rates for those with late stage carcinomas are poor.

In its more aggressive form, transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with PC. Local invasions typically involve the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that a majority of newly diagnosed prostate cancer patients will have metastases at the time of initial diagnosis.

Many studies have shown that there exists a specific metastasis suppressor role for p53, a well-known tumor suppressor protein, in PC (reviewed in [5]). Initial experimental results using an in vivo mouse model of PC metastasis demonstrated that loss of p53 function can lead to the development of metastases that seed from relatively small numbers of cells within the primary tumor 6. Subsequent studies demonstrated that although p53 mutations in human primary PC tissues are heterogeneous and relatively infrequent, they occur at significant levels in metastatic disease, ranging from 21%-30% mutation frequency in lymph node metastasis to higher than 90% mutation frequency in androgen-insensitive disseminated disease [7-12]. This pattern of mutations suggests that only a few cells harboring p53 mutation in the primary tumor can seed metastases that clonally expand at distant sites. Consequently, there is a need for improved research tools, diagnostic tools and therapies, useful for the diagnosis, treatment and prevention of PC and metastasis associated with transformed prostate cells.

SUMMARY OF THE INVENTION

The present invention overcomes the problems and disadvantages associated with current strategies and designs and provides new diagnostic, therapeutic and research tools, and methods based on certain proteins related to testes-specific, vespid and pathogenic proteins (RTVP). The invention also relates to compositions and kits comprising the RTVP gene, the RTVP polypeptide and active fragments thereof, and antibodies thereto.

One embodiment of the invention is directed to isolated nucleic acids comprising the sequence of the RTVP gene. The gene may comprise the entire sequence of RTVP, all or part of the sequence. Further, the invention includes the RTVP polypeptide encoded therein, and active portions thereof. Genes may be functionally linked to vectors such as plasmid or viral vectors and be capable of expression in a suitable host.

Another embodiment of the invention is directed to recombinant cells containing nucleic acid segments that encodes RTVP polypeptides and portions thereof. Cells may be eukaryotic or prokaryotic, and may express the protein or act simply as biological containers of the gene sequence.

Another embodiment of the invention is directed to antibodies reactive against the RTVP protein and to antibodies that may be reactive to antigenically active portions thereof. Antibodies may be polyclonal or monoclonal, recombinant or synthetic. A further embodiment of the invention is directed to hybridomas that express antibodies to the RTVP polypeptide or to antigenic portions thereof.

Another embodiment of the invention is directed to the receptor of RTVP protein, and to compositions and methods useful for the treatment of neoplastic diseases such as prostate cancer and related metastasis. A further embodiment is directed to the gene for the receptor protein as well as to associated promoter and other transcription or translation controlling sequences. A further embodiment includes antibodies to the RTVP receptor protein which may also be useful for the treatment of neoplastic diseases such as prostate cancer and metastasis.

Another embodiment of the invention is directed to kits for the detection of prostatic disease. Kits comprise all or characteristic portions of the RTVP gene or the RTVP polypeptide sequence, or to antibodies to either the polypeptide or nucleic acid sequences, and are useful for detection of disease.

Another embodiment of the invention is directed to nucleic acid sequences that comprise the anti-sense of the RTVP gene or representative portions thereof. Sequences may be useful in compositions to for the treatment of prostatic disease by reducing or shutting down RTVP expression in cells.

Another embodiment of the invention is directed to compositions comprising RTVP or RTVP receptor polypeptides, or active portions thereof, as pharmaceutical compositions. Compositions may be useful in therapy, prophylaxis, diagnosis, or as research tools, and may further comprise pharmaceutically acceptable carriers for use in the treatment or prevention of diseases such as prostate cancer and metastatic disease.

Another embodiment of the invention is directed to methods for stimulating the immune system such as, for example, cytokines and growth factors, by administering composition of the invention to patients. Compositions may be administered in a therapeutically safe and effective dose to humans and other mammals in the form of pills, tablets, powder, liquid or combinations thereof.

Other embodiments and advantages of the invention are set forth in part in the description which follows, and in part, will be obvious from this description, or may be learned from the practice of the invention.

DESCRIPTION OF THE FIGURES

FIG. 1A Nucleic acid sequence of mouse RTVP-1 (SEQ ID NO:1).

FIG. 1B Comparison of mouse (SEQ ID NO:2) with human (SEQ ID NO:3) RTVP-1 amino acid sequence.

FIGS. 5A1-5E RTVP-1 suppression of tumor growth and metastasis.

FIGS. 6A1-6C Local and systemic immune response in AdmRTVP-1 treated tumors.

FIG. 7B Bystander effect of p53 gene therapy.

FIGS. 7C1-7C12 p53 regulation of prostate cancer.

FIG. 18A1-18A10 Immune cell infiltration in 178-2BMA orthotopic tumors.

FIG. 18B1-18B3 Immune response in animals with 178-2BMA orthotopic tumors.

DESCRIPTION OF THE INVENTION

Figures 1, 2A:
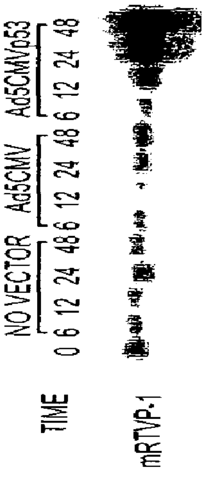
FIGS. 2A1-2E Identification of RTVP-1 regulation by p53.

As embodied and broadly described herein, the present invention is directed to nucleic acid sequences encoding RTVP or the RTVP receptor protein, or active portions thereof, to RTVP and RTVP receptor polypeptides and functional portions thereof, to antibodies to thereto, and to compositions, kits and methods based on RTVP for the treatment, prevention and detection of disease, and specifically prostate disease, in mammals.

It has been shown that there exists a specific and established association between loss of p53 function and prostate cancer metastasis. Recent studies demonstrated that specific p53 mutations are clonally expanded in metastatic prostate cancer [11] and that a pattern of aberrant p53 expression in primary tumors, termed "clustered p53 staining," has significant prognostic value in predicting recurrence following radical prostatectomy [12,13]. It is generally considered that the nature of functional alterations which occur in cells containing p53 mutations specifically facilitates metastatic seeding, survival, and growth at distant metastatic sites. These alterations likely result, in part, from aberrant regulation of genes under the transcriptional control of p53 that have previously been shown to mediate apoptosis [1,14-17] and anti-angiogenic activities [18-22].

Surprisingly, it has been discovered that certain proteins related to testes-specific, vespid and pathogenic proteins (RTVP), and specifically mouse RTVP-1, are up-regulated by p53 in mouse prostate cancer cells. Proteins which are Related to Testes-specific, Vespid and Pathogenic proteins include those protein with homology to mammalian testes-specific proteins (e.g. TPX1), plant pathogenesis-related proteins (e.g. PR-protein such as subtype 1, PR-1b), vespid venom allergan proteins (antigen 5), or combinations thereof. Homology means that there is a relevant degree of similarity in the amino acid sequence between a polypeptide of the invention and one or more of the proteins mammalian testes-specific proteins, plant pathogenesis proteins and vespid venom allergan antigen 5, or in the respective gene sequences. Relevant homology means that the degree of amino acid sequence similarity is about 35% or greater, preferably about 45% or greater, more preferably about 60% or greater, and even more preferably about 75% or greater. Homology can be determined directly by sequencing the polypeptide of interest and comparing it with the known sequence, or experimentally by methods well know to those or ordinary skill in the art. Homology can be determined using, for example, blastp queries at default settings for amino acid homology determinations, and using blastn queries at default settings for nucleic acid homology determinations. Although the human RTVP gene was previously isolated [23,24], the functional significance of RTVP expression in any biological context has not previously been reported. Further, human RTVP is significantly homologous (about 50% or greater) to mouse RTVP-1 (Table 1). Loss of RTVP-1 expression is associated with mouse and human prostate cancer metastasis. Importantly, it has also been discovered that mRTVP-1 has pro-apoptotic, anti-angiogenic, and immunostimulatory activities. This multifaceted role for mRTVP-1 in suppression of prostate cancer metastasis has also been shown using adenoviral-vector-mediated mRTVP-1 expression to suppress growth and metastasis of prostate cancer in vivo. Further, based on the presence of an extracellular protruding domain of the RTVP protein and the results of media-transfer experiments, therapeutic control of disease may also be achieved by targeting an RTVP receptor protein.

Accordingly, the present invention is directed to a novel gene, RTVP, which is under the regulation of p53 in human and mouse prostate cancer cells and potentially other normal and malignant cells. The sequence was identified using cell lines derived from mouse prostate cancer generated by the mouse prostate reconstitution model system. Briefly, a primary mouse prostate cancer cell line (148-1PA) was infected with an adenoviral vector containing wild-type human p53 and with a control virus without any added exogenous genes. The p53-induced and control mRNAs were used to generate cDNAs, and a fragment was isolated using differential display-PCR (DD-PCR) techniques. This fragment encoded the novel mouse protein, RTVP-1. Upon sequencing the DD-PCR fragment, it was determined that this mouse cDNA may be related to the human mRNA for RTVP-1 protein/human glioma pathogenesis-related protein, as there appeared to be significant homology at the nucleotide level.

Full-length cDNA for RTVP-1 was cloned using a cDNA library prepared from 148-1PA cells. Its expression pattern in normal mouse prostate cancer tissues was further analyzed. Expression for this protein at the mRNA level appeared to be relatively low in most tissues examined including prostate, yet mRNA levels were exceedingly high for colon, spleen and lung. Further analysis of primary and metastatic mouse prostate cancer cell lines by Northern blotting indicated that RTVP was present at low levels in primary tumor-derived cell lines, but appeared to be down regulated in metastasis-derived cell lines. This indicated the possibility that loss of expression of this gene may be selected for during metastatic progression of prostate cancer.

To determine the potential functional significance of RTVP, adenoviral vectors containing the mouse RTVP cDNA were constructed and this adenoviral vector together with a control vector for apoptotic activity were tested in the p53 null human colon cancer cell line, H1299. The data clearly indicated that, at MOI of 100, more than 2-fold increase in annexin V positive cells was seen in RTVP infected cells relative to the same MOI of a control virus that expressed only the beta-galactosidase gene. Additional studies were also consistent with RTVP stimulated apoptosis. These data indicated that a novel p53-regulated gene that is involved in apoptosis in prostate cancer and potentially other malignancies had been identified. That sequence, and the peptide it encodes, provide potential diagnostic/prognostic tools and/or therapeutic targets in clinical malignancies and growth disorders.

Accordingly, one embodiment of the invention is directed to nucleic acids that comprises all or one or more portions of the sequence of RTVP, to peptides derived from these sequences, and to sequences complementary thereto. The nucleic acid sequence that encodes mouse RTVP-1 protein is shown in FIG. 1*a* (SEQ ID NO: 1). The amino acid sequence of the mouse RTVP-1 protein (SEQ ID NO. 2) is shown in FIG. 1*b*. Nucleic acids of the invention may be single-stranded or double-stranded and composed of DNA, RNA or PNA, or another appropriate nucleic acid, polypeptide or functionally similar backbone structure. Single stranded nucleic acids may be in the form of a sense strand or an antisense strand. Further, although the human RTVP gene sequence is know (GenBank DNA database accession number X91911), RTVP genes of the invention may be derived from other mammals such as, for example, mice, rats or any rodent, cattle, sheep, goats, pigs, horses, canines, felines, and most any other non-human mammal.

Nucleic acids according to the invention include isolated (e.g. purified) and recombinant nucleic acid sequences comprising SEQ ID NO: 1, or a portion of SEQ ID NO: 1 encoding all or one or more active fragments of the RTVP polypeptide. Nucleic acids containing conserved regions of sequences and nucleic acids encoding open reading frames and conserved domains within open reading frames are typically sufficient to represent or contain identifiable portions of RTVP such as functional and antigenic portions. Nucleic acids may comprise additional sequences such as RTVP-specific promoters, activator and repressor sites, and enhancers for modulation of expression of sense or antisense messages, recombination sequences for gene targeting, selectable markers for transfections, or replication origins for passage in a host such as bacteria, virus, eukaryotic cells or yeast. A further embodiment of the invention includes RTVP-specific promoters which modulation transcription (e.g. by differential methylation of promoter sequences) of RTVP in normal, pre-malignant and malignant cell. These promoters can be functionally coupled to anti-neoplastic genes to treat or prevent cell proliferative disorders such as, for example, tumors, prostate cancer, and metastatic disease. Nucleic acids may be packaged in a viral vector such as, for example, a retroviral, a vaccinia or an adenoviral vector. In one embodiment, the sequence may be part of a homologous recombination vector designed to recombine with another sequence. The invention further includes vectors comprising the nucleic acid sequences of the invention, polypeptides expressed by these vectors, and recombinant cells comprising these vectors.

Another embodiment of the invention is directed to all or an effective fragment of a RTVP polypeptide comprising all or part of the amino acid sequence encoded from the nucleic acid sequence of FIG. 1*a* (see FIG. 1*b*; SEQ ID NO. 2), such as, for example, exonic fragments, fragments encoded in open reading frames of RTVP genes, conserved domains of the polypeptide or the nucleic acid, and p53 binding sites. Specifically, the invention includes isolated polypeptides comprising all or active fragments of the polypeptide encoded in an RTVP gene, and monoclonal and other antibodies to these peptides.

Nucleic acids and polypeptides or proteins (RTVP and receptor proteins) according to the invention may be used as a diagnostic or therapeutic tool in the detection, treatment or prevention of diseases, such as neoplastic disorders (e.g. malignant tumors, metastatic disease) and cell or tissue growth disorders. For example, one embodiment of the invention is directed to diagnostic aids or kits for the detection of neoplasia in a patient. Detection kits may comprise RTVP nucleic acid sequences or RTVP polypeptides whose presence or absence in the sample would be indicative of the presence of a disease such as, for example, prostate cancer or a prostate metastasis. Samples which can be analyzed include samples of biological fluids (e.g. blood, plasma, interstitial fluid, urine, cerebrospinal fluid) and samples of biological tissue (e.g. surgical biopsy).

Another embodiment of the invention is directed to antibodies specifically reactive against polypeptides and proteins and fragments thereof of the invention. Antibodies may be polyclonal or monoclonal of any isotype (e.g. IgA, IgD, IgE, IgG1, IgG2a, IgG2b, or IgM), or antibody fragments (e.g. Fab, Fv), humanized antibodies, or recombinant or synthetic antibodies (e.g. variable region fragments). Further, the invention comprises hybridomas that express antibodies specifically reactive against polypeptides of the invention.

Another embodiment of the invention is directed to a method for treating a neoplastic or growth disorder comprising administering a pharmaceutically effective amount of a composition comprising an RTVP polypeptide, polypeptide fragment or ligand of a polypeptide. Such compositions maybe anti-angiogenic, be used to modulate (e.g. increase or decrease) cytokine or other immune system regulatory proteins or their activity, induce apoptosis, and/or stimulate a cell or humoral response. For example, in cell growth disorders such as prostate cancer and other neoplasias, cytokine expression may be improperly turned off (e.g. methylated) in malignant or pre-malignant cells. As such, these gene products may also be useful as a diagnostic for malignancy. Alternatively, compositions of the invention may be useful in, for example, auto-immune disease to turn on genes whose activity may be improperly reduced or turned off (e.g. by methylation). Further, polypeptides of the invention may stimulate apoptosis and are useful as therapeutics to treat and prevent neoplasia such as, for example, tumors, metastasis and any uncontrolled cell growth. A further embodiment of the invention comprises the RTVP promoters which are differentially modulated (e.g. by methylation) and regulate expression.

The polypeptide or polypeptide fragment, or a ligand to the polypeptide may be administered by injection, pulmonary absorption, topical application and delayed release. The composition may further comprise a pharmaceutically acceptable carrier such as water, alcohols, salts, oils, glycerols, fatty acids, starchs, saccharides, polysaccharides or combinations thereof. More than one carrier may be used together to create a pharmaceutical with desirable properties. A further embodiment of the invention comprises vaccines for the treatment and/or prevention of neoplastic disease. Vaccines may comprise antibodies reactive against polypeptides and/or polypeptide fragments of the invention, of the polypeptides themselves. Vaccines comprise therapeutically effective doses of the therapeutic agent, which may be the polypeptide or polypeptide fragment, or an antibody or collection of antibodies which bind or are otherwise reactive thereto.

Another embodiment of the invention is directed to nucleic acids derived or based on the sequence of RTVP such as, for example, the sequence of SEQ ID NO: 1, useful in treatment or diagnosis and in diagnostic kits. Treatment may involve using the sequences, or effective parts thereof, in gene therapy, including gene ablation, gene expression and gene suppression, such as antisense suppression. Diagnosis may involve genotypic analysis of samples to determine the existence and expression levels of the genes. Nucleic acids of the present invention may be used in various treatment and research modalities, including gene replacement, gene targeting, antisense inhibition, antisense blocking, genetic ablation and gene silencing. Gene replacement involves replacing a copy of a defective gene with another copy by homologous recombination. Gene targeting involves the disruption of a cellular copy of a gene by homologous recombination. Gene targeting refers to a process of introducing a nucleic acid construct into a cell to specifically recombine with a target gene in the cell. The nucleic acid construct inactivates the gene after targeting. Inactivation may be by introduction of termination codons into a coding region or introduction of a repression site into a regulatory sequence. Antisense inhibition exploits the specificity of hybridization reactions between two complementary nucleic acid chains to suppress gene expression. If a cloned gene is engineered so that only the opposite DNA strand is transcribed, the resultant RNA may hybridize to the sense RNA and inhibit gene expression. Antisense blocking refers to the incorporation into a cell of expression sequences which direct the synthesis of antisense RNA to block expression of a target gene. Antisense RNA hybridizes to the mRNA of the target gene to inhibit expression. Genetic ablation (gene knockout) refers to one process of silencing a gene in a cell. Genetic ablation (gene knockout) may be performed after a cell is selected for use or by selecting a cell already comprising a genotype with the proper genetic ablation. Ablation of the gene encoding RTVP, for example by pre-transcriptional inhibition (such as homologous recombination with endogenous recessive oncogenes) or post transcriptional inhibition (such as the expression of antisense oncogenes to suppress translation) may be useful. Gene silencing is performed by transfecting cells with nucleic acids which cause genetic ablation or by antisense suppression. The silencing process may include processes such as gene targeting or antisense blocking.

Another embodiment of the invention is directed to methods to modulate a cytokine activity with effective amounts of RTVP protein or active portions thereof. Cytokines whose activity may be up regulated (e.g. through demethylation) include the type 1 or THI cytokines such as, for example, INF-alpha, beta and gamma, TNF-gamma, IL-2, IL-6, IL-12, and the death domain proteins such as Fas, and their ligands (i.e. receptors) such as Fas-ligand and Trail. Cytokines whose activity may also be modulated by RTVP include the type 2 or TH2 cytokines such as, for example, IL-1β, IL-4, IL-10. Increased or decreased expression or function of cytokines is an important aspect of RTVP therapy and has implications for both cancer and non-cancer therapy. One of the more important cytokines induced is IFN-gamma, wherein RTVP-1 is believed to be inducing a methylation change in the IFN-gamma promoter, which is normally completely methylated and therefore silent in normal cells. Differential methylation of these and RTVP promoter sequences can be used diagnostically to detect as well as therapeutically to treat neoplastic disease. Alternatively, in specific cancer cells including prostate cancer, global perturbations in methylation can silence tumor suppressor genes such as, for example, p16, and also lead to demethylation of genes that (i) produce a more malignant cell and is therefore selected during progression (e.g. such as caveolin-1), or (ii) make the cell susceptible to apoptosis when an appropriate stimulus is provided. In prostate cancer, the IFN-gamma gene promoter may be demethylated and therefore susceptible to induction. RTVP-1, which is expressed in normal prostatic epithelial cells, then becomes lethal to the cell by activating IFN-gamma which leads to direct cell killing or indirect cell killing via an immune response. Upon isolation of the RTVP receptor, ligands could be identified that could activate the RTVP-1 pathway, turn on IFN-gamma or another cytokine, which may be cancer and immune cell specific and thereby specifically target cancer cells.

Another embodiment of the invention is directed to receptor protein for RTVP proteins such as an RTVP-1 receptor, which is important for stimulating downstream activities of RTVP-1 Downstream activities includes apoptosis and stimulation of cytokine expression and apoptosis through stimulation of an immune response, which offers an extracellular therapeutic approach.

The following examples illustrate embodiments of the invention, but should not be view as limiting the scope of the invention.

EXAMPLES

Example 1

Identification of mRTVP-1 as a p53 Target Gene

Over the last decade, numerous studies have established p53 mutations as being paramount to the development and progression of various malignancies. The p53 tumor suppressor protein has been associated with various antitumor activities that include growth suppression, apoptosis, and anti-angiogenic activities. The majority of human tumor mutations decrease the sequence-specific DNA binding and transcriptional activity of the p53 protein [26]. Today the large and expanding list of genes under the transcriptional control of p53 have been reported and it has been estimated that 200-300 genes are under the transcriptional regulation of p53 [27]. To date, the number of reported p53-regulated genes is approximately 80 [28].

Figures 2, 2A:
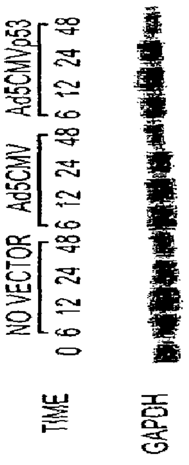
Figures 1, 2B:
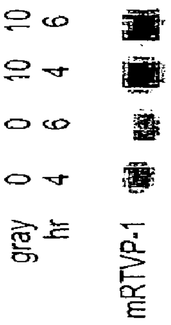
Figures 2, 2B:
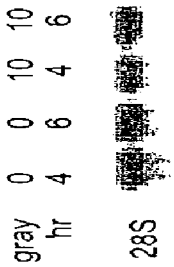
Figures 1, 2C:
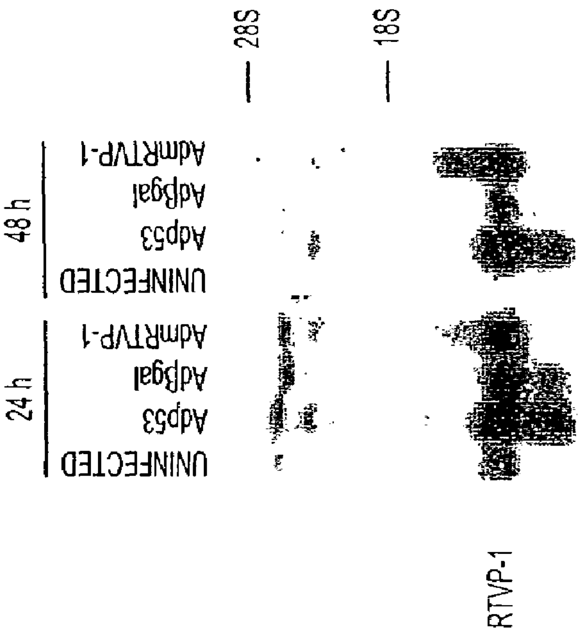
Figures 2, 2C:
Figure 2D:
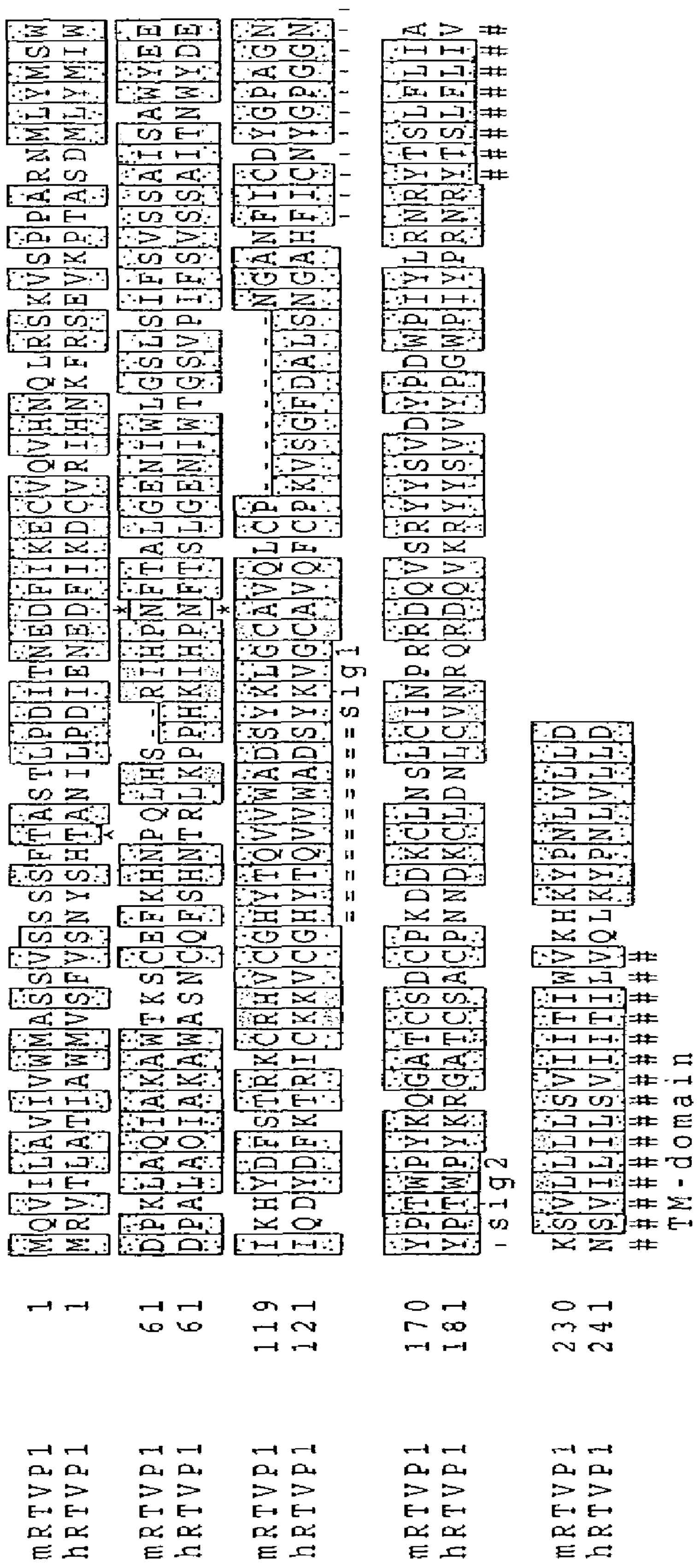
Figure 2E:
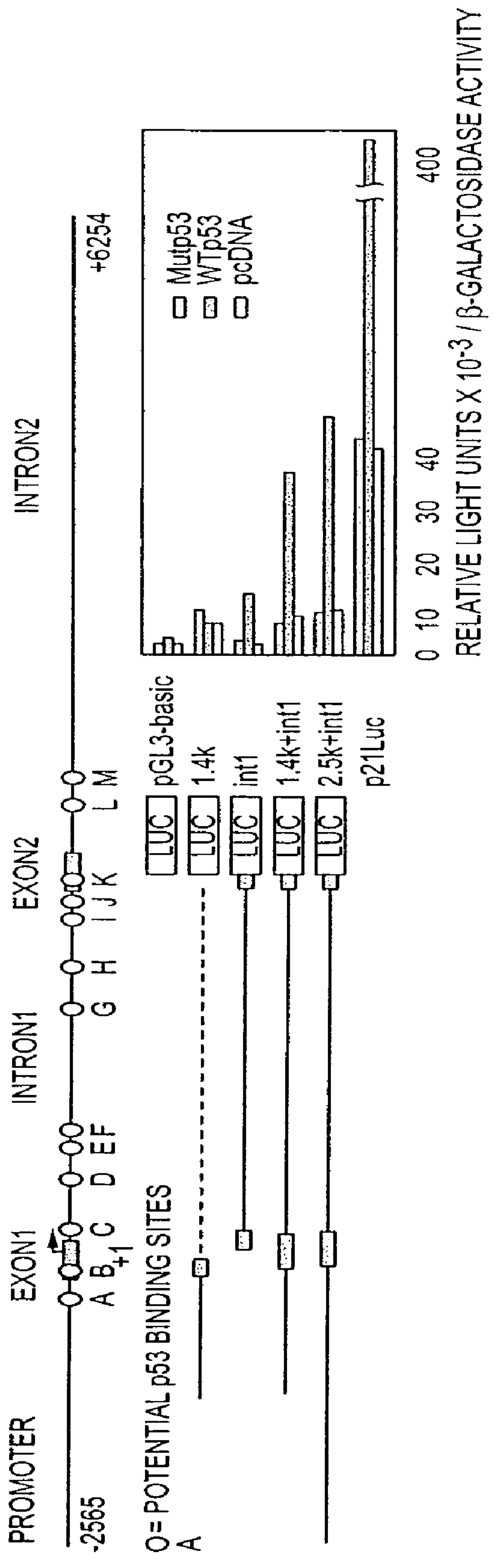
Figure 3A:
FIGS. 3A-3H In situ hybridization of human prostate cancer.
Figure 3B:
Figure 3C:
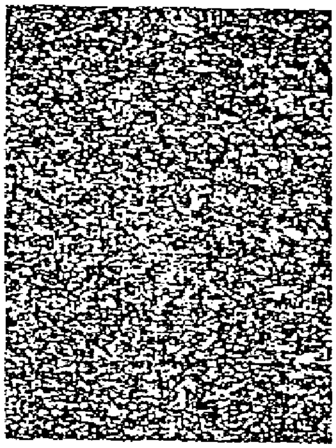
Figure 3D:
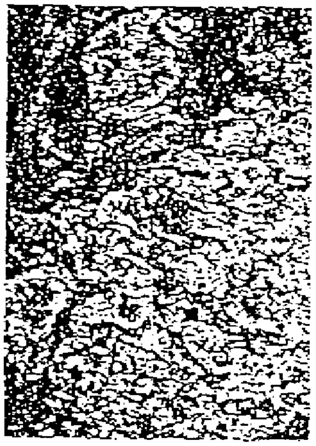
Figure 3E:
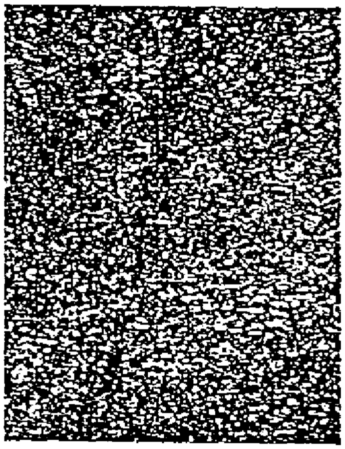
Figure 3F:
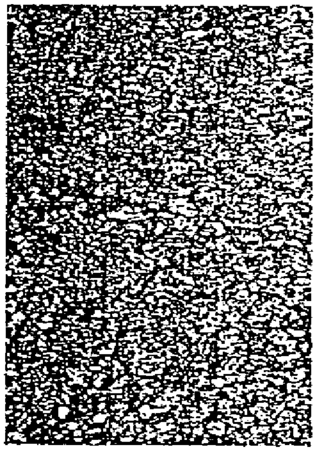
Figure 3G:
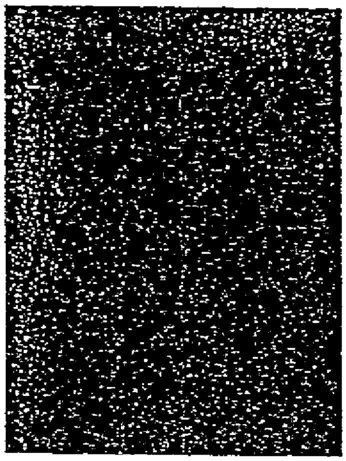
Figure 3H:
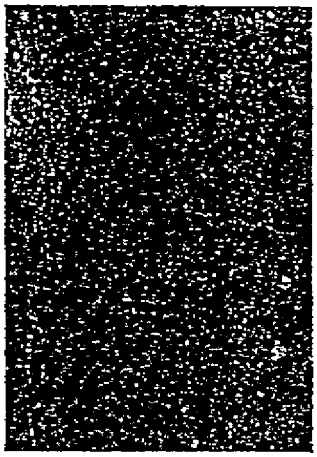

To identify prostate cancer-related genes under the transcriptional regulation of p53, a model system was established using adenoviral vector delivery of wild-type p53 compared to β-gal or an empty cassette together with differential display-PCR. Using this approach, numerous sequences were isolated that were known to be under p53 control including cyclin G, epoxide hydrolase, and MDM2. In addition, genes were isolated that had not been previously associated with p53 regulation. One of the sequences identified encoded the mouse homologue for RTVP-1 [23,24]. Briefly, mouse prostate cancer cell lines were grown in DMEM with 10% fetal bovine serum (FBS). Human prostate cancer cell lines Tsu-Prl and LNCaP were grown in RPMI 1640 with 10% FBS and PC3 in Kaighn's modified am's F12 with 10% FBS. For adenoviral infections the vector was diluted to the appropriate multiplicity of infection (MOI) in serum free medium with 0.1% bovine serum albumin and left in contact with the cells for 4 h followed by fresh media. Differential display-PCR was as previously described [34] using RNA isolated from AdCMVp53 or Ad gal infected 148-1PA cells. Differentially expressed PCR band was subcloned, sequenced and used to screen mouse and human cDNA and mouse genomic libraries. Mouse mRTVP-1 cDNA was inserted into the plasmid pcDNA3.1 (Invitrogen, Carlsbad, Calif.) for transfection studies or used to prepare an adenovirus (AdmRTVP-1) as previously described [35,36] Genomic DNA containing mRTVP-1 promoter fragments were subcloned into the luciferase reporter vector pGL3-luc (Promega, Madison, Wis.) and equimolar concentrations transfected into Tsu-PR1 cells with Lipofectamine along with mutant or wild type p53 expressing plasmids [37]. Luciferase activity was standardized to a cotransfected—galactosidase plasmid as previously described [38]. Freshly isolated rat aortic ring slices were infected with adenoviral vector in serum free endothelial medium (EGM-2, BioWhittaker, Walkersville, Md.) for 3 h then cultured in Matrigel for 48 h to allow for endothelial cell sprouting as described [39]. Protein lysates were prepared with TNES lysis buffer [50 mM Tris (pH 7.5); 2 mM EDTA, 100 mM NaCl, 1% NP40, 20 μg/ml aprotinin, 20 μg/ml leupeptin and 1 mM PMSF], separated on 10-12% polyacrylamide-SDS gels and electrophoretically transferred to nitrocellulose membrane for western blotting. Antibodies included Bad and phospho-Bad (New England Biolabs, Beverly, Mass.); BID (R&D Systems, Minneapolis, Minn.); Bax, Bcl-2, Bcl-XL, caspase 6 and cytochrome c (BD-Pharmingen/Transduction Labs, San Diego, Calif.); and caspases 3, 7, 8, 9, and 10 (Oncogene Research Products, Boston, Mass.). β-actin monoclonal antibody (Sigma, St Louis, Mo.) was used as a loading control. Rabbit polyclonal antibody to peptides 59-71 of the mRTVP-1 protein was affinity purified. RTVP-1 cDNA was originally cloned from human glioma tissue and was subsequently reported to be expressed in differentiated macrophages [25]. Shown in FIG. 2 is the identification of RTVP-1 regulation by p53. Kinetic analysis of mRTVP-1 mRNA expression following infection of the p53 null mouse prostate cancer cell line 148-1PA [6] with no adenoviral vector, control adenoviral vector (Ad5CMV), or p53 expressing Ad5CMVp53 [42] (FIG. 2*a*). Induction of mRTVP-1 by γ-irradiation in p53 wild type prostate cancer cell line RM9 [43] (FIG. 2*b*). Induction of RTVP-1 by Ad5CMVp53 in the human prostate cancer cell line Tsu-Prl relative to uninfected, control Adβgal, or AdmRTVP-1 (FIG. 2*c*). Comparison of deduced protein sequence for mouse and human RTVP-1 (FIG. 2*d*). Identical amino acids are enclosed in dark boxes, conserved amino acid substitutions are lightly shaded, and gaps in the alignment by a -. A potential N-glycosylation site is indicated by a *. The putative signal sequence precedes a cleavage site indicated by the symbol ^. Two conserved regions known as extracellular protein signature motifs 1 and 2 (sig1 and sig2) and a transmembrane domain (TM) are indicated. Schematic of the genomic sequence with potential p53 binding sites and fragments used for luciferase constructs (FIG. 2*e*). The mRTVP-1 genomic sequence was from clone 163K10 from the mouse RPCI-21 PAC library [44]. DNA sequence analysis identified multiple p53 consensus binding sites (RRRCWWGYYY n RRRCWWGYYY, SEQ ID NO. 4; where R=purine, Y=pyrimidine, W=A or T and n=1-22 nucleotides) as well as recognition sites for IFNβ, NFκβ, GM-CSF and AP-1 (not shown). The luciferase activity was determined 24 h after transfection of mRTVP-1-luciferase expression vectors into Tsu-Prl cells along with a β-gal plasmid for standardization and a plasmid expressing mutant p53 (shaded boxes), wild type p53 (solid boxes), or control plasmid (open boxes). A p21 promoter luciferase plasmid was used as a positive control for p53 activation.

Using the differential display-PCR fragment as a probe, it was determined that mRTVP-1 mRNA (~1.1 kb transcript) was significantly induced at 24 and 48 hours after AdCMVp53 infection in the p53 null mouse prostate cancer cell line 148-1 PA and by γ-irradiation in mouse prostate cancer RM-9 cells that contain wild-type p53. Additional studies showed that RTVP-1 (~0.8 and 1.3 kb transcripts) expression was also induced following AdCMVp53 infection in the human prostate cancer cell line Tsu-Prl. Differential display-PCR fragment was used to screen a cDNA library generated from 148-1 LMD mouse prostate cancer cells and isolated multiple cDNAs containing the complete ORF of mRTVP-1 that encodes 255 amino acids with 68% identity to the human RTVP-1 protein. Notably, mRTVP-1 contains two short in-frame deletions of two amino acids (PH) at positions 86, 87 and a nine-amino acid deletion (KVSGFDALS SEQ ID NO. 5) from amino acid 158 through 166 relative to human RTVP-1. Both mouse and human proteins contain a putative N-linked glycosylation site and a hydrophobic region near the carboxy terminus. Interestingly, both proteins also contain putative N-terminal signal peptides and extracellular protein signature motifs, which suggests that both proteins are potentially located on the surface of the cell membrane or even secreted. The mRTVP-1 cDNA was also used to isolate genomic mRTVP-1 and sequenced 2.5 kb of promoter sequences as well as exon 1, intron 1 and exon 2 of the mRTVP-1 gene. Multiple putative p53 binding sites were documented in the mRTVP-1 promoter and intron 1, with at least 13 in intron 1. In co-transfection studies using mRTVP-1-luciferase expression vectors, specific induction of luciferase activity by exon 1-intron 1 sequences following co-transfection mRTVP-1-Int1-luc with wild-type p53 in Tsu-Prl cells was demonstrated. When 1.4 or 2.4 kb of promoter sequences was included upstream of exon 1-intron 1, a significant increase in p53 inducibility, but also basal promoter activity was observed. These results suggest that one or more putative p53 binding sites within intron 1 are mediating p53 regulation of mRTVP-1.

Example 2

RTVP-1 mRNA Levels are Down-Regulated in Prostate Cancer Metastases

Figures 1, 5A:
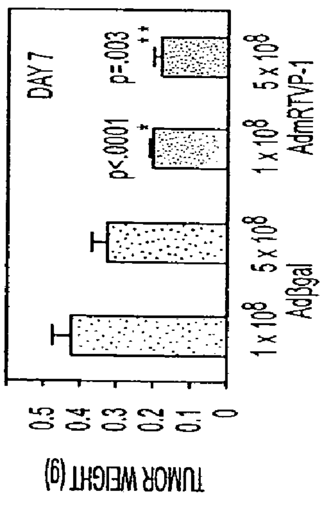
Figures 2, 5A:
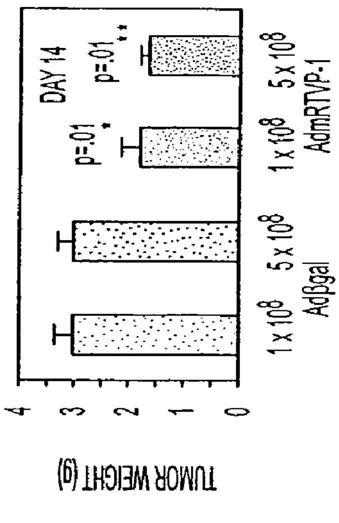
Figures 1, 5B:
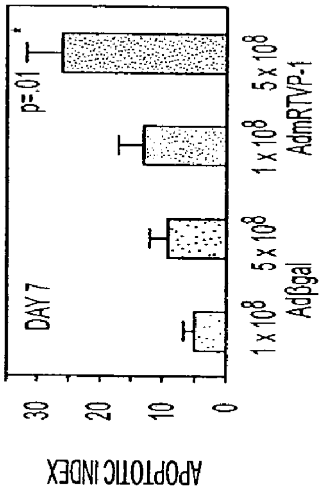
Figures 2, 5B:
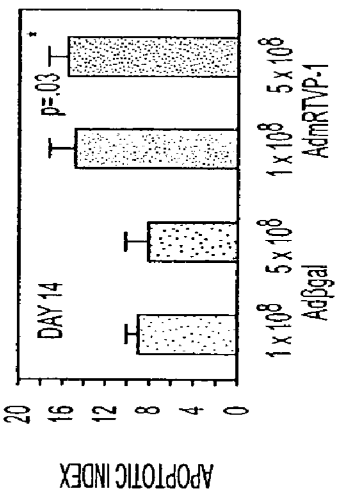
Figure 5C:
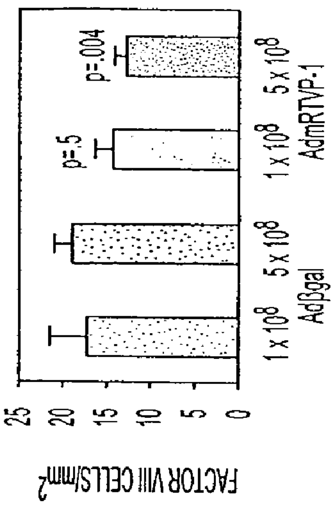
Figure 5E:
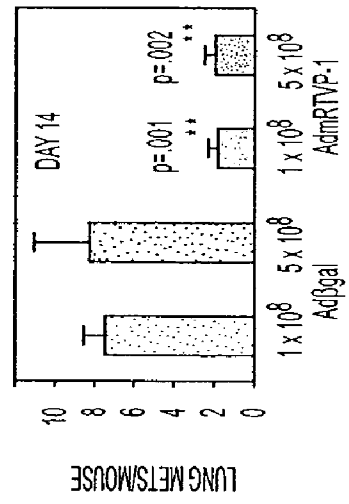
Figures 1, 5D:
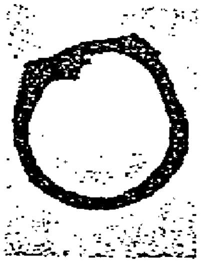
Figures 2, 5D:
Figures 3, 5D:
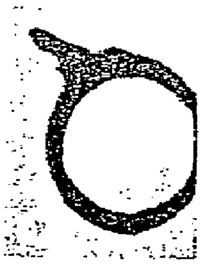

Having demonstrated that mRTVP-1 is induced by p53; it was next determined the mRNA expression profile of RTVP-1 in mouse and human prostate cancer tissue specimens by in situ hybridization (FIG. 3). Briefly, normal mouse prostate or prostate cancer developed in the mouse prostate reconstitution model with strain 129/SV wild type, heterozygous or homozygous for p53 knockout [6] were used for in situ hybridization. Human primary prostate cancers and lymph node metastatic deposits as well as histologically normal prostate were obtained at radical prostatectomy. The specimens were frozen in liquid nitrogen immediately after surgical removal and 6-μm sections cut with a cryostat. Sections were air-dried and fixed in a solution containing 3 parts 4% paraformaldehyde, 4 parts ethanol and 3 parts glacial acetic acid for 20 min. Anti-sense cRNAs of mRTVP-1 (400 bases) and hRTVP-1 (256 bases) or corresponding sense RNA probes were made by run-off transcription of the vector pCR2.0 (Invitrogen) with SP6 or T7 polymerase, respectively using the DIG-RNA labeling kit (Roche Diagnostics Corp. Indianapolis Ind.). The sections were prehybridized in 50% formamide, 5×SSC, 5× Denhardt's solution, 250 μg/ml yeast t-RNA, 4 mM EDTA and 1 mg/ml salmon sperm DNA at 37C° for 60 min and hybridized in the prehybridization buffer (without the salmon sperm DNA) containing 2.5 to 10 ng/μl DIG-labeled cRNA probes at 48 C° overnight. Sections were then rinsed in 4×SSC (2×10 min), 2×SSC (10 min) and 1×SSC (10 min) and 0.1×SSC (30 min at 48 C). The DIG-labeled RNA was detected with mouse anti-DIG IgG followed with a DIG conjugated antibody to the mouse IgG Fab fragment and finally anti-DIG IgG conjugated with fluorescein (Roche). Sections from normal prostate and cancer as well as metastatic cancer deposits were always processed in parallel under the same conditions and using the same batches of probes and reagents. Sections were evaluated under a fluorescence microscope and the RTVP-1 mRNA levels were scored according to the relative fluorescence intensities (see Table 2) as −: No signal detectable, +: weak; ++ moderate, and +++: strong. Statistical analysis using Mann-Whitney U test was performed to determine the significance of the differences in the fluorescence scores in different tissues.

Shown in FIG. 3 is RTVP-1 mRNA expression in mouse (m) and human (h) prostatic tissues as demonstrated by in situ hybridization with fluorescent riboprobes. RTVP-1 mRNA is expressed in the basal and glandular epithelial cells of both normal mouse and human prostates (mNP-AS or hNP-AS respectively). Cancer cells expressed a moderate level of RTVP-1 mRNA in both mouse (mPCa-AS) and human (hPCa-AS) primary prostate tumors. In contrast, much lower levels of RTVP-1 mRNA were shown in the metastatic deposits of both mouse (mPCa-Met AS) and human (hPCa-Met AS) lymph nodes. Sections from both mouse and human prostate cancers that were incubated with the sense riboprobes gave rise to minimal signal (mPCa-S and hPCa-S). Original magnification: 200×.

Semi-quantitative in situ hybridization analysis of a panel of mouse (not shown) and human prostate cancer tissue specimens revealed abundant RTVP-1 mRNA levels in normal human prostatic basal and secretory epithelial cells and in primary tumor cells (Table 2). However, RTVP-1 mRNA levels were significantly reduced in metastases relative to normal prostatic epithelium or primary prostate cancer cells. Immunohistochemical analysis for p53 protein using the criteria of clustered staining [10] revealed a general trend toward association of reduced RTVP-1 mRNA and aberrant p53 protein accumulation, yet the data were more consistent with independent inactivation of RTVP-1 (Table 2). Extensive sequencing analysis of RTVP-1 cDNAs isolated from prostate cancer cell lines and tissues did not reveal RTVP-1 gene mutations suggesting other mechanisms of gene inactivation (data not shown).

These data show that endogenous RTVP-1 mRNA expression is specifically reduced in metastatic mouse and human prostate cancer. Interestingly, RTVP-1 mRNA levels were abundant in normal prostate epithelial cells and in primary prostate cancer cells suggesting that the RTVP-1 gene is active in the absence of high levels of p53 protein. Therefore, it appears that p53-independent pathways can regulate RTVP-1 expression under both normal and abnormal conditions. Immunostaining analysis of p53 protein showed a trend towards an association between aberrant accumulation and reduced RTVP-1 mRNA levels yet the data were more consistent with independent inactivation of RTVP-1 gene expression. Initial sequencing analysis of cDNAs isolated from malignant prostate cancer cells failed to reveal any structural mutations in the RTVP-1 coding region.

Example 3

Pro-Apoptotic Activities of mRTVP-1 are Mediated Through the Mitochondrial Pathway To analyze the biological activities of mRTVP-1, a series of human prostate cancer cell lines (Tsu-Prl, LNCaP, and PC3) and the human lung cancer cell line, H1299, were infected with AdmRTVP-1 or Adβgal. Western blotting analysis demonstrated high levels of intracellular mRTVP-1 protein by 48 hours after infection.

Figure 4A:
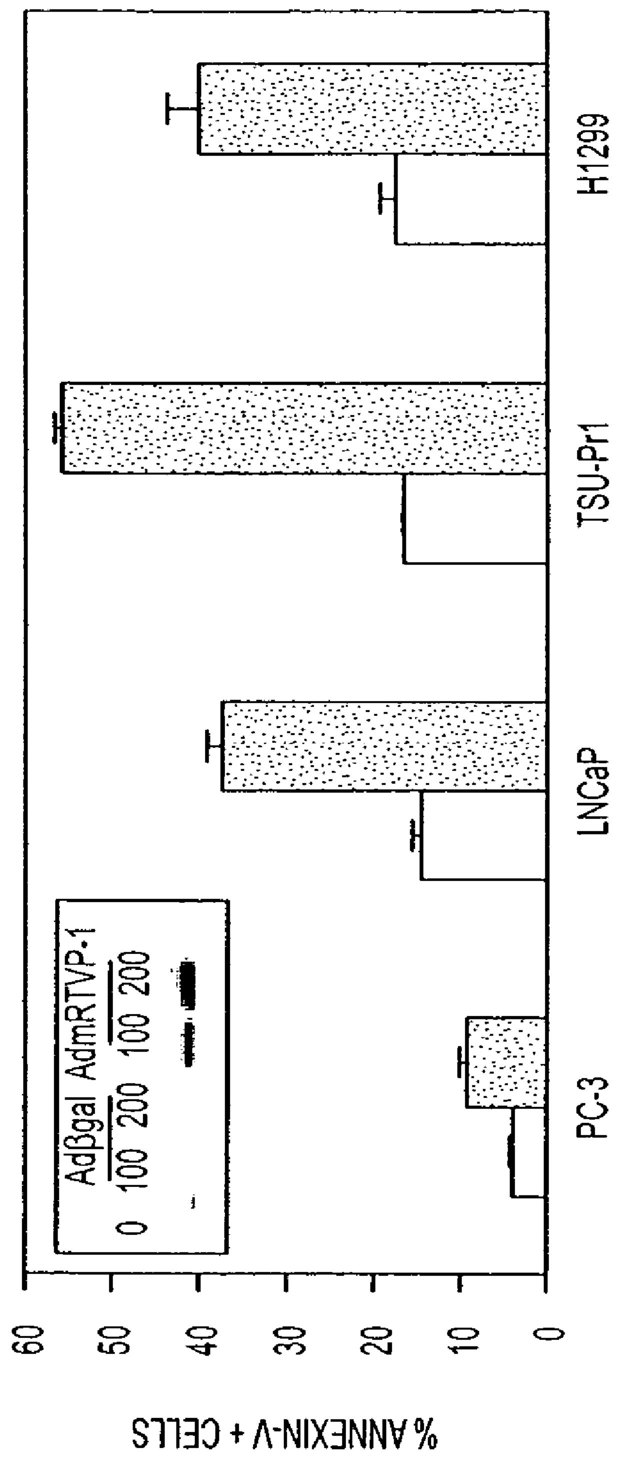
FIGS. 4A-4C mRTVP-1 induction of apoptosis through mitochondrial death pathway.
Figure 4C:
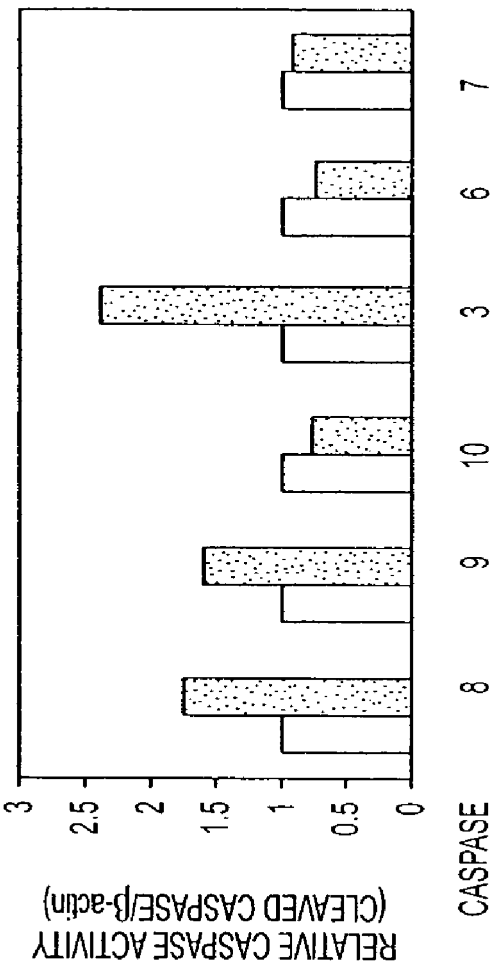
Figure 4B:
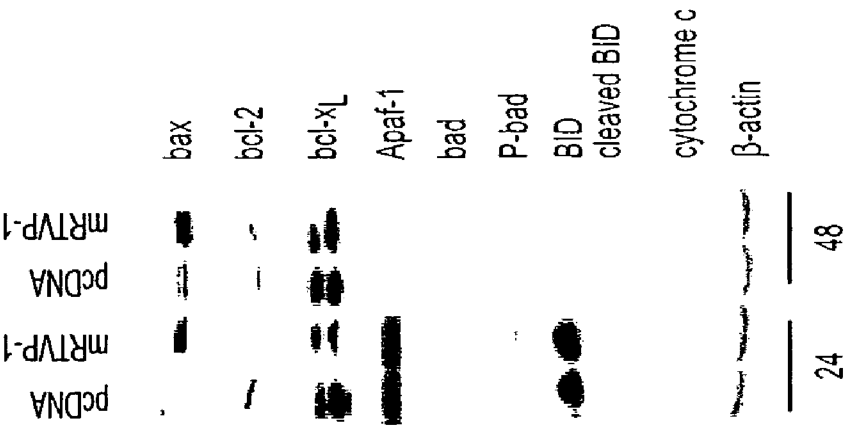
Figures 4, 5D:
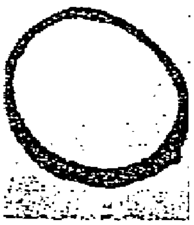

As shown in FIG. 4, mRTVP-1 induces apoptosis through mitochondrial death pathway. Apoptosis was determined by annexin V binding and flow cytometry on cells infected with Adβgal (open boxes) or AdmRTVP-1 (closed boxes) at an MOI of 100 as described 38 (FIG. 4*a*). Protein levels of mRTVP-1 in Tsu-Prl cells were determined by western blotting. Western blotting for bcl family member proteins and cytosolic cytochrome c in LNCaP lysates following transfection with control plasmid pcDNA or pmRTVP-1 (FIG. 4*b*). Relative caspase activity was determined by densitometric analysis of western blots of the cleavage product for each specific caspase relative to β-actin as a loading control in lysates from LNCaP cells following infection with Adβgal (open boxes) or AdmRTVP-1 (closed boxes) (FIG. 4*c*).

Thus, AdmRTVP-1 induced apoptosis as evidenced by significant increases in annexin V positivity, DNA fragmentation (not shown) and DAPI staining (not shown). To further probe the mechanisms of apoptosis induction by mRTVP-1, the expression of bcl-2 family proteins in LNCaP cells was evaluated following mRTVP-1 transfection. These results demonstrated that mRTVP-1 expression led to increased levels of pro-apoptotic bax, bad and activated BID, but down regulation of anti-apoptotic bcl-2 and bcl-XL. Increased levels of cytosolic cytochrome c were also demonstrated following mRTVP-1 transfection, indicating activation of the mitochondrial apoptosis pathway. The activation of specific caspases was also analyzed using western blotting with antibodies specific for the activated forms of the initiation caspases 8, 9, and 10 and effector caspases 3, 6 and 7. The results indicated that AdmRTVP-I infection was capable of inducing activation of caspases 8, 9 and 3 relative to control Adβgal infection in LNCaP cells. Following mRTVP-1 transfection, apoptosis was also induced with frequencies and characteristics similar to that observed following infection with AdmRTVP-1 (not shown).

Example 4

Adenoviral Vector-Mediated mRTVP-1 Expression Suppresses Prostate Cancer Growth and Metastasis To determine possible therapeutic activities induced by overexpression of mRTVP-1 in vivo, an orthotopic mouse model of metastatic prostate cancer was used. Briefly, orthotopic tumors were initiated by injecting 5000 178-2BMA cells into the dorsolateral prostate of 129/SV mice. Seven days later when the tumors achieved an average wet weight of 25 mg they were injected with adenoviral vector in a volume of less than 25 μl. Six to ten animals were injected with each dose. At the indicated times, tumor tissue was weighed then frozen in liquid nitrogen or fixed in 10% formalin and processed for paraffin embedding. Apoptosis was determined by TUNEL labeling as previously described [40]. Mean vessel density and tumor cell infiltrate quantitation was essentially as previously described [41] using monoclonal Rat-anti mouse antibodies for CD8, CD4, F4/80, TNF-(BD-Pharmingen), as well as polyclonal antibodies to NOS2 (BD-Pharmingen) and Factor VIII-related antigen (Dako, Carpinteria, Calif.). Spontaneous metastases to the lung were microscopically counted after overnight fixation in Bouin's solution [41]. NK activity was determined by lysis of YAK cells by splenocyte derived cells as previously described [41] Serum IL-12 was determined by immunoassay (Biosource, Camarillo, Calif.). All mice were maintained in facilities accredited by the American Association for Accreditation of Laboratory Animal Care and all experiments conducted in accordance with the principles and procedures outlined in the National Institutes of Health's Guide for the Care and Use of Laboratory Animals.

Figures 5, 5D:
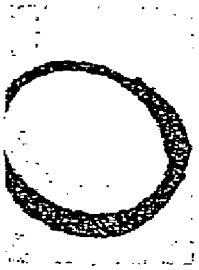

As indicated, seven days following orthotopic inoculation of 178-2BMA cells, tumors were injected with either $1\times10^8$ or $5\times10^8$ PFU of AdmRTVP-1 or Adβgal. At 7 and 14 days post vector treatment, tumors were recovered from animals and both primary tumors and their metastases were analyzed extensively. As shown in FIG. 5, mRTVP-1 suppresses tumor growth and metastasis. Wet weight of orthotopic 178-2BMA tumors treated with Adβgal at $1\times10^8$ PFU (open box) or $5\times10^8$ PFU (hatched box) or with AdmRTVP-1 at $1\times10^8$ PFU (shaded box) or $5\times10^8$ PFU (closed box) on day 7 (left panel) or day 14 (right panel) after tumor cell inoculation. * $P\leqq0.05$;  $P\leqq0.01$ (FIG. 5***a*). Apoptotic index as determined by TUNEL labeling (symbols as in α) (FIG. 5*b*). The tumor microvessel density (symbols as in a) as measured by factor VIII staining was decreased by high dose AdmRTVP-1 (FIG. 5*c*). Rat aortic ring slices were incubated with the indicated dose of adenoviral vector then placed in Matrigel and 48 h later photographed (FIG. 5*d*). Spontaneous lung metastases from adenoviral vector treated orthotopic tumors in animals was determined on day 21 (symbols as in α) (FIG. 5*e*).

AdmRTVP-1 significantly suppressed the growth of primary tumors compared to control Adβgal vector injections at both vector doses when evaluated at both time points ($P<0.01$). Additional analysis indicated that increased apoptotic levels were likely responsible for the growth suppressive effects of AdmRTVP-1 as significant increases in TUNEL labeling were documented in tumors treated with $5\times10^8$ PFU of AdmRTVP-1 at both day 7 ($P=0.028$) and day 14 ($P=0.015$). Further, a significant reduction ($P=0.004$) in the density of Factor VIII-positive tumor associated endothelium was also associated with the higher dose of AdmRTVP-1 when day 14 tumors were analyzed. In an independent in vitro angiogenesis assay, the rat aortic ring sprouting assay, treatment with AdmRTVP-1 inhibited endothelial cell sprouting compared to Adβgal. To evaluate potential antimetastatic effects of mRTVP-1 in the 178-2 BMA orthotopic model, the extent of lung metastases in AdmRTVP-1-treated and control Adpgal-treated animals was analyzed on day 14 after tumor initiation. Both doses of AdmRTVP-1 significantly suppressed spontaneous lung metastases compared to Adβgal infection ($P\leqq0.002$), indicating that mRTVP-1 associated activities lead to suppression of growth and spontaneous metastatic activities of orthotopically grown mouse prostate cancer. These results suggest that mRTVP-1 mediated pro-apoptotic and anti-angiogenic activities likely played a role in suppression of tumor growth and metastasis.

Example 5

Expression of mRTVP-1 Induces a Local and Systemic Anti-Tumor Immune Response

Figures 5, 5D, 6:
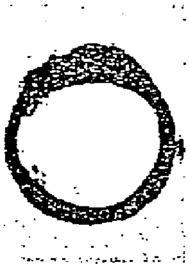
Figures 1, 6A:
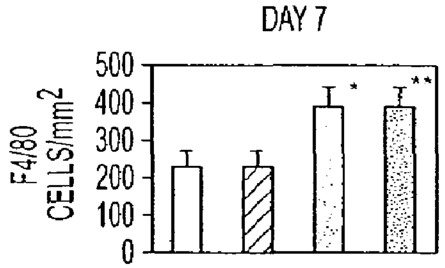
Figures 2, 6A:
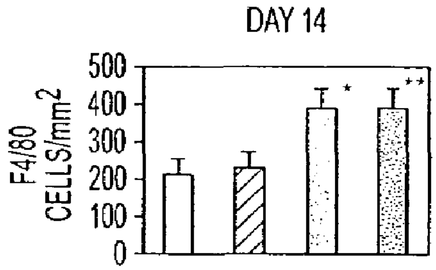
Figures 3, 6A:
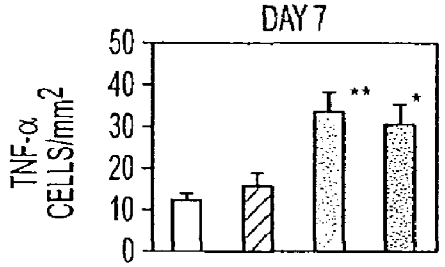
Figures 4, 6A:
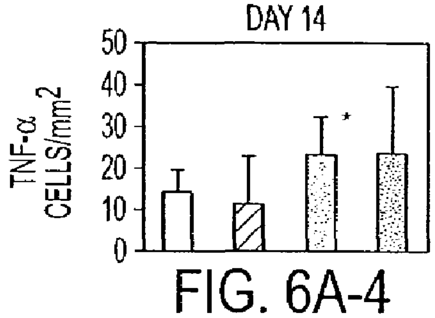
Figures 5, 6A:
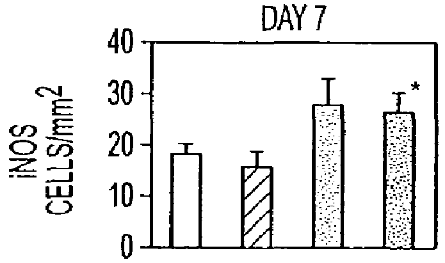
Figures 6, 6A:
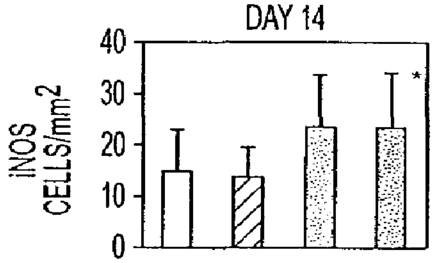
Figures 6, 6A, 7:
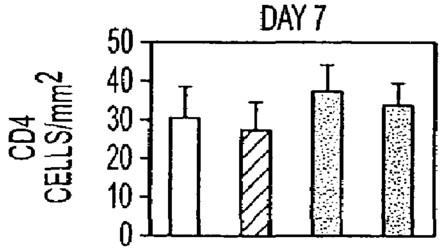
Figures 6, 6A, 7, 8:
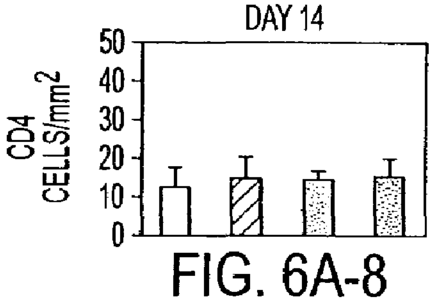
Figures 6, 6A, 7, 8, 9:
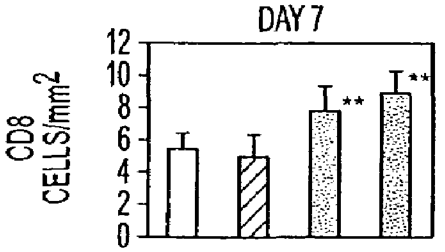
Figures 6, 6A, 7, 8, 9, 10:
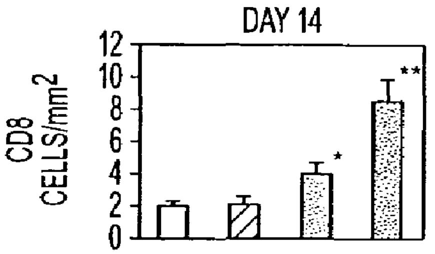
Figure 6C:
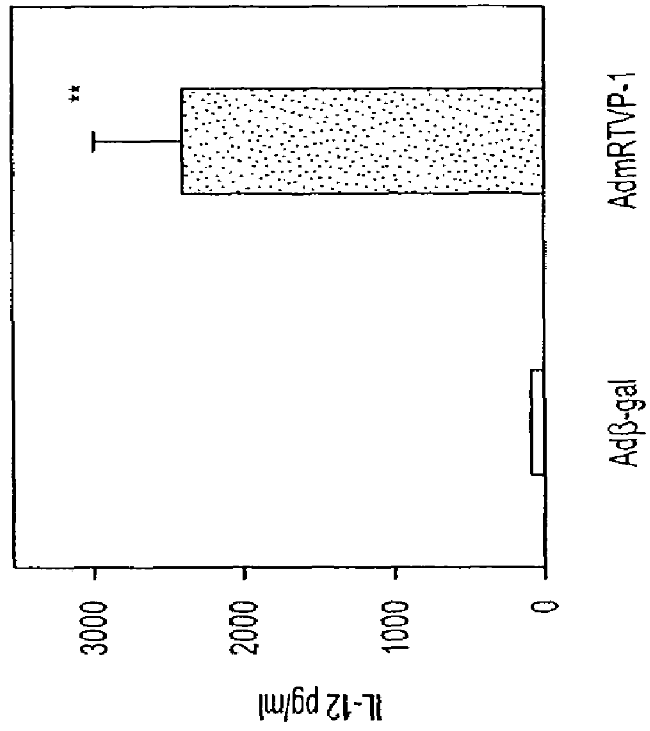
Figure 6B:
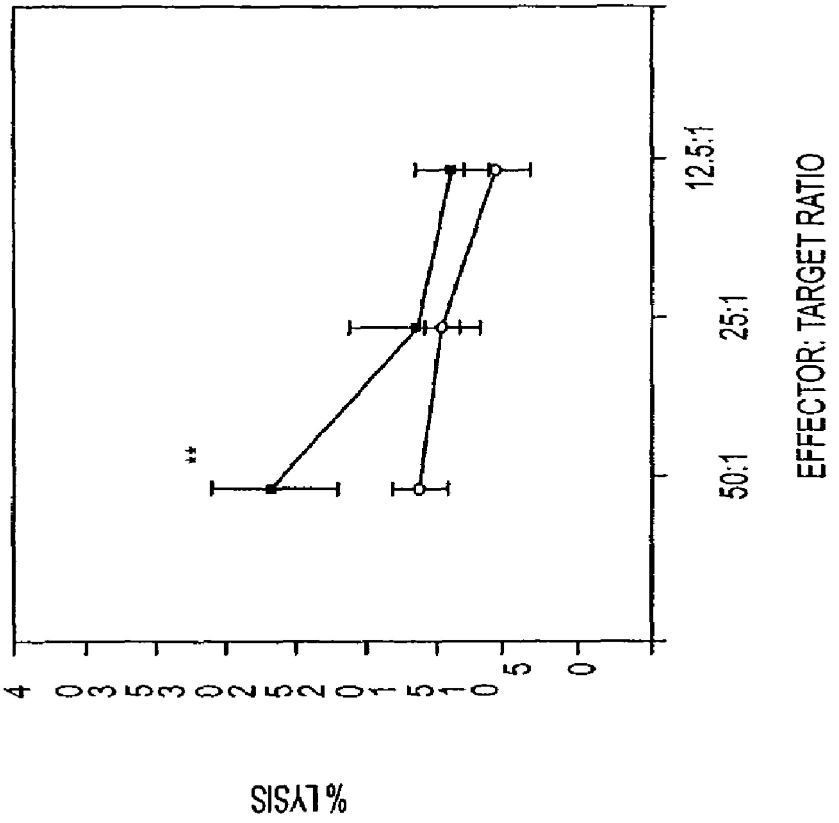

To further explore the underlying mechanisms responsible for mRTVP-1 mediated antimetastatic activities, local and systemic immune responses was analyzed in animals with AdmRTVP-1 treated tumors compared to control Adβgal infected tumors. Local and systemic immune response in AdmRTVP-1 treated tumors are shown in FIG. 6. Immunohistochemical detection of F4/80, TNF-α, NOS2 (iNOS), CD4 and CD8 positive cells were quantitated by image analysis and expressed as positive cells per $mm^2$ (symbols as in FIG. 5) (FIG. 6*a*). NK activity two days after vector inoculation. (■=AdmRTVP-1 treated animals, ○=Adβgal treated animals) (FIG. 6*b*). Serum IL-12 levels from animals sacrificed on day two or three after vector inoculation (FIG. 6*c*).

The results indicated significant increases in the density of tumor-associated F4/80-positive macrophages (P=0.03 for $1\times10^8$ PFU and P=0.01 for $5\times10^8$ PFU) and CD8+T cells (P=0.004 at both doses) in AdmRTVP-1 infected tumors relative to control Adβgal infected tumors at both day 7 following vector treatment. Significant infiltrates of tumor associated macrophages and CD8+ T cells persisted for both doses at 14 days post treatment (P=0.017 and P=0.02 for macrophages and P=0.018 and P=0.0005 for CD8+ T cells for $1\times10^8$ PFU and $5\times10^8$ PFU respectively) indicating sustained immunostimulatory activities. Analysis of activation markers associated with tumor associated F4/80-positive macrophage indicated that AdmRTVP-1 specifically increased NOS-2 and TNF-α activities in this cell type. To determine whether mRTVP-1 overexpression in the primary tumor elicited a systemic immune response splenocytes were isolated from mice bearing AdmRTVP-1 and control Adβgal infected tumors and used for analysis of NK activities. Significantly increased NK activities were demonstrated two days post vector injection in the mice with AdmRTVP-1 treated tumors compared to mice with Ad gal treated tumors (P=0.01, unpaired t test at E:T of 100:1 and 0.004 at 50:1) In addition, a significant increase in serum levels of IL-12 (P=0.001) was seen in animals with AdmRTVP-1 treated tumors relative to Adβgal two to three days following vector injection.

Overall, these results specify that mRTVP-1 as a p53-induced gene and is involved in apoptosis-mediated tumor suppressor activities. Although there are numerous studies that have documented the tumor suppressing activities of p53 in various systems and clear evidence has been found for a role for p53 as a tumor suppressor gene in human cancer, the reported antimetastatic activities of p53 have thus far remained somewhat ambiguous. Certainly, the induction of apoptosis and suppression of angiogenesis could inhibit metastatic spread, yet in some malignancies such as prostate cancer the clear association of loss of p53 function with metastasis suggests the existence of additional p53-mediated anti-metastatic activities. These results show an additional role for p53 as an antimetastatic gene as an inducer of mRTVP-1, which in turn can generate an antitumor immune response that is manifest locally as well as systemically. One previously published report indicated that p53 could induce the CX3C chemokine, fractalkine, raising the possibility that p53 effector genes are also involved in immune cell stimulation [29]. It is of interest that RTVP-1 and fractalkine share some structural characteristics as predicted by the amino acid sequence. Both proteins have a consensus signal peptide and a putative transmembrane domain region. As fractalkine has been shown to be present in a soluble form [30,31] it appears that this chemokine and potentially RTVP-1 exist as both membrane bound and soluble forms, and are therefore capable of paracrine activities. In the case of fractakine, paracrine functions appear to be limited to chemotactic and pro-adhesion activities [30,31]. However, the paracrine functions of mRTVP-1 appear to generate widespread immunostimulatory activities in vivo that include the induction of F4/80-positive macrophage and CD8+ T cell infiltrates within the primary tumor; the induction of splenocyte derived NK activities; and the generation of increased serum IL-12 levels.

The uptake of increased numbers of apoptotic bodies by antigen presenting cells could lead to the activation of specific immune cells including macrophages that were shown to be increased within primary tumors following AdmRTVP-1 treatment. Activated macrophages or potentially activated dendritic cells could secrete IL-12 (shown to be increased in serum) and lead to increased systemic NK activities. Alternatively, membrane bound or soluble mRTVP-1 could directly activate immune cell activities. Since RTVP-1 expression has been associated with differentiated macrophages, [25] a role for RTVP-1 as a cytokine-like molecule is likely.

These data clearly demonstrate that p53 can induce expression of RTVP-1 in prostate cancer cells in vitro and that overexpression of mRTVP-1 has widespread immunostimulatory activities in vivo. Further, stress-related p53 induction may induce RTVP-1 levels sufficiently to induce immune cell activities that counteract the growth and progression of human prostate cancer.

These studies are relevant for prostate cancer as the development of effective treatments for prostate cancer are frustrated by the natural history of the disease. The biological and clinical potential of most individual cancers is uncertain and in many cases the disease will not progress to clinical significance. However, experimental and clinical studies indicate that prostate cancer can and may metastasize early in the course of the disease from relatively small foci [32,33]. Although localized prostate cancer is potentially curable with radical prostatectomy or irradiation therapy, there are no curative therapies for metastatic prostate cancer. As shown by these results, expression of mRTVP-1 in prostate cancer through adenoviral vector transfer can induce local cytotoxicity through direct and indirect apoptosis while simultaneously initiating a local and systemic anti-tumor immune response. Thus, RTVP-based therapy may be useful as a new weapon against both prostate cancer and metastatic disease.

Example 6

Mechanism of action of RTVP-1

Figure 7A:
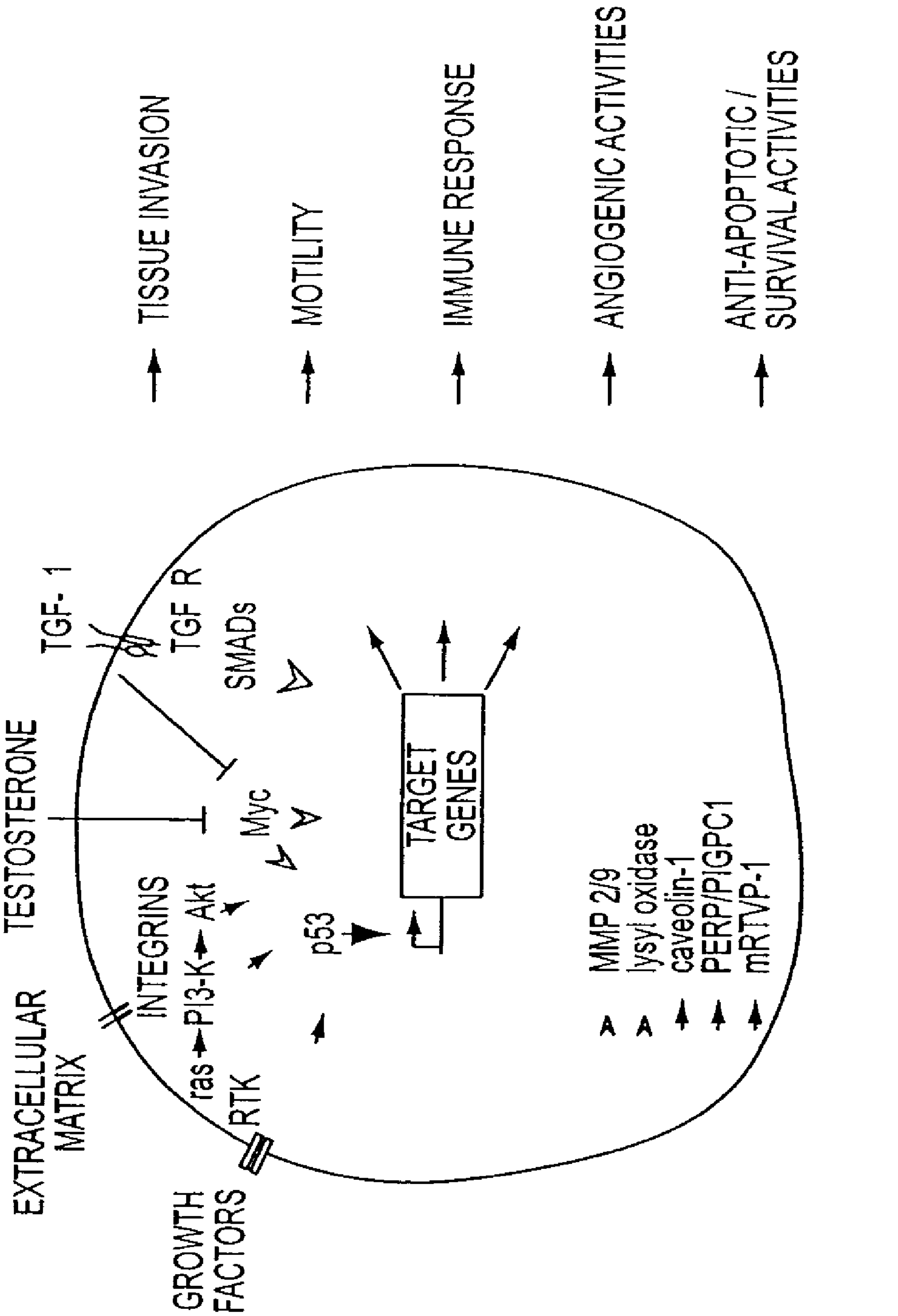
FIG. 7A Molecular pathways in prostate cancer.
Figures 4, 7C:
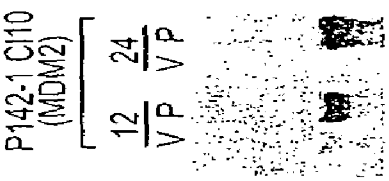
Figures 3, 7C:
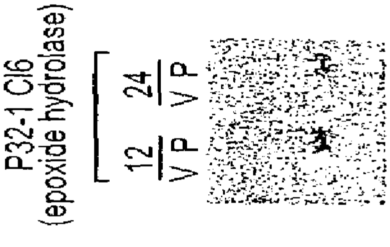
Figures 2, 7C:
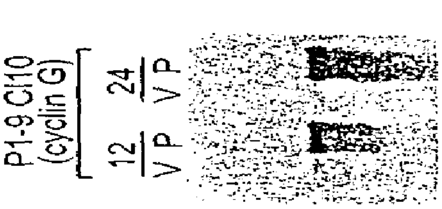
Figures 1, 7C:
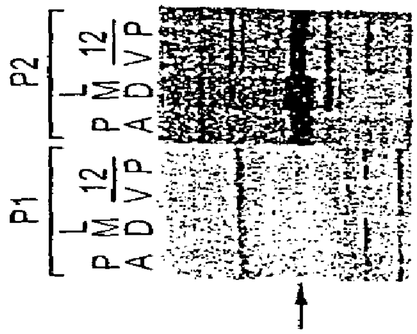
Figures 6, 7C:
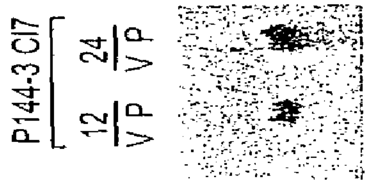
Figures 5, 7C:
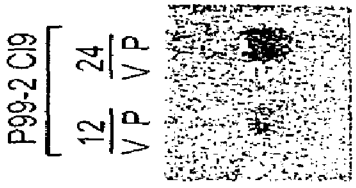
Figures 7, 7C:
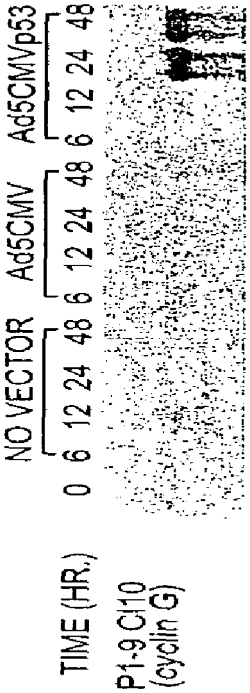
Figures 7, 7C, 8:
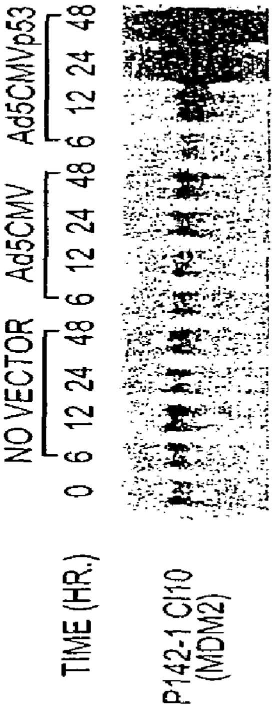
Figures 7, 7C, 8, 9:
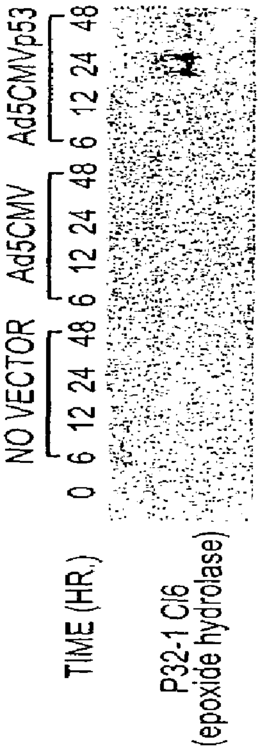
Figures 7, 7C, 8, 9, 10:
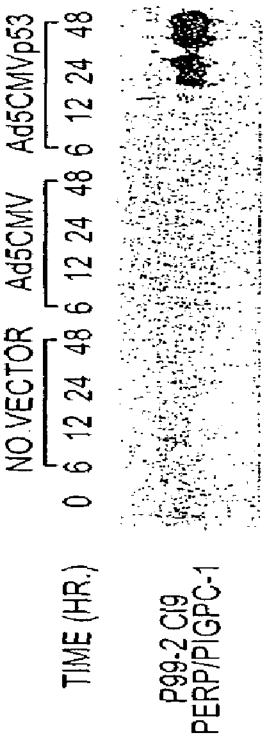
Figures 7, 7C, 8, 9, 10, 11:
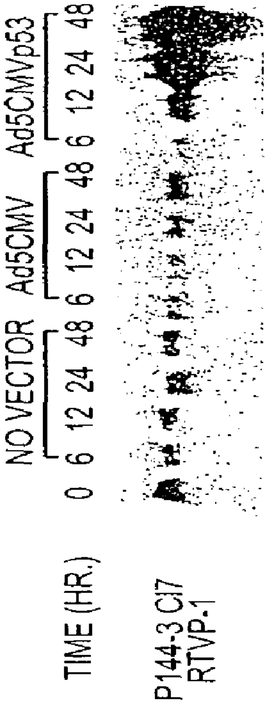
Figures 7, 7C, 8, 9, 10, 11, 12:
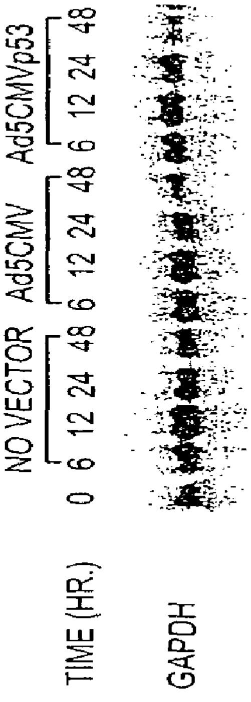
Figure 8:
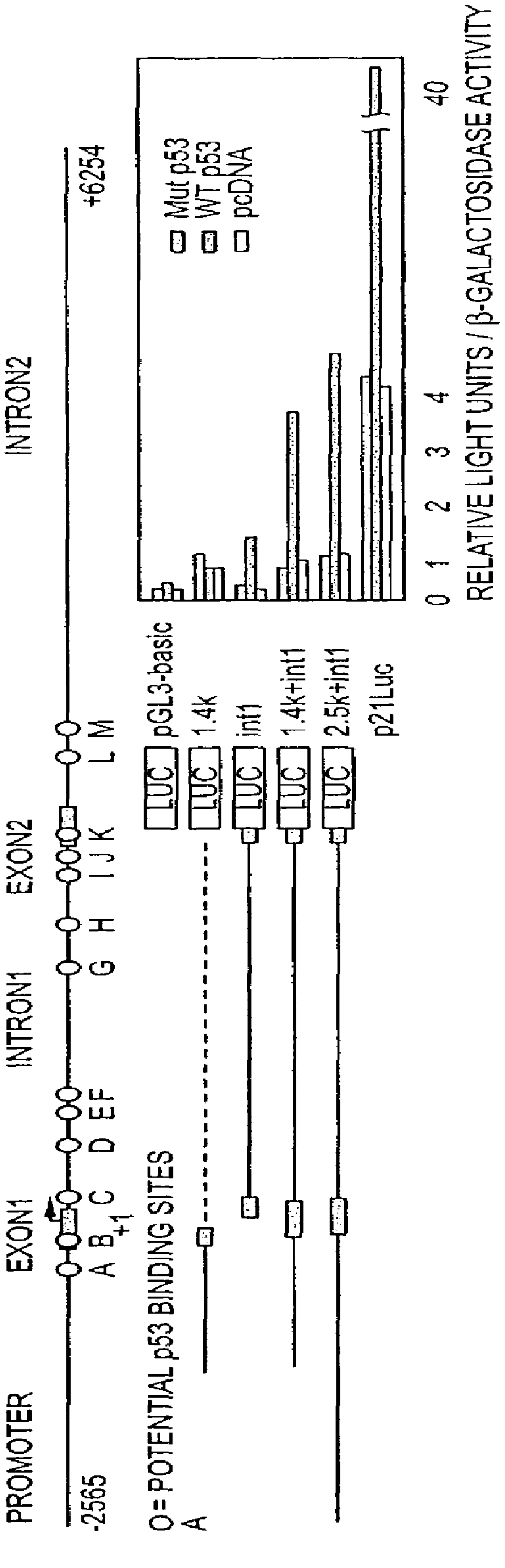
FIG. 8 Wild-type p53 regulation of mRTVP-1 promoter constructs.
Figure 9A:
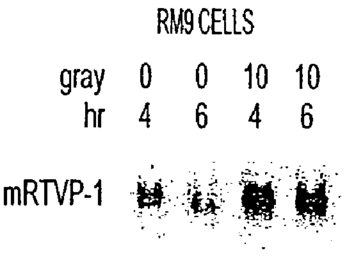
FIGS. 9A-9E Induction of mRTVP-1.
Figure 9B:
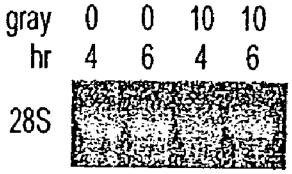
Figure 9C:
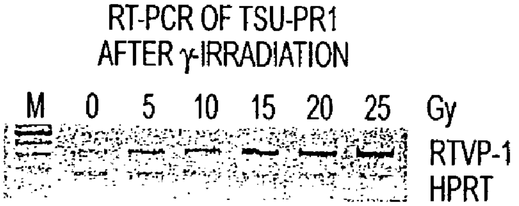
Figure 9D:
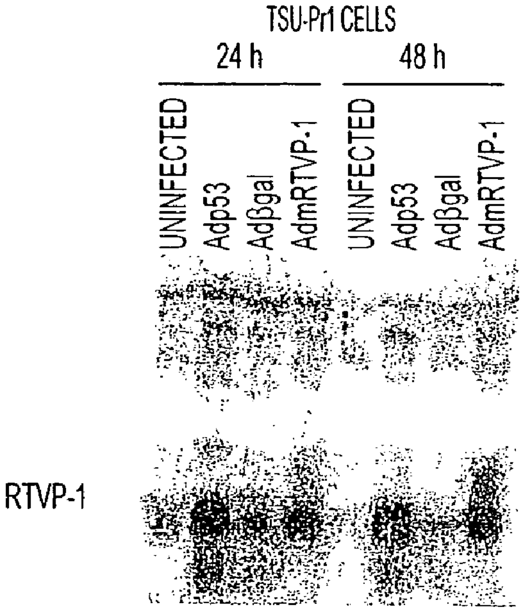
Figure 9E:
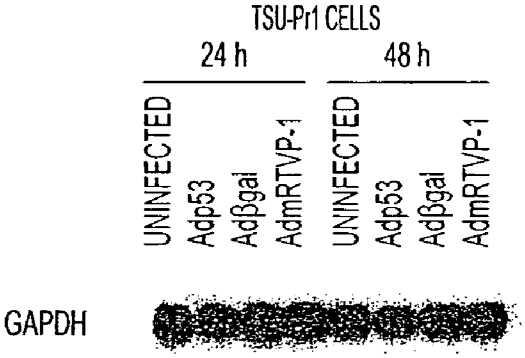
Figure 10C:
FIGS. 10A-10D RTVP-1 expression in mouse and human tissue.
Figure 10A:
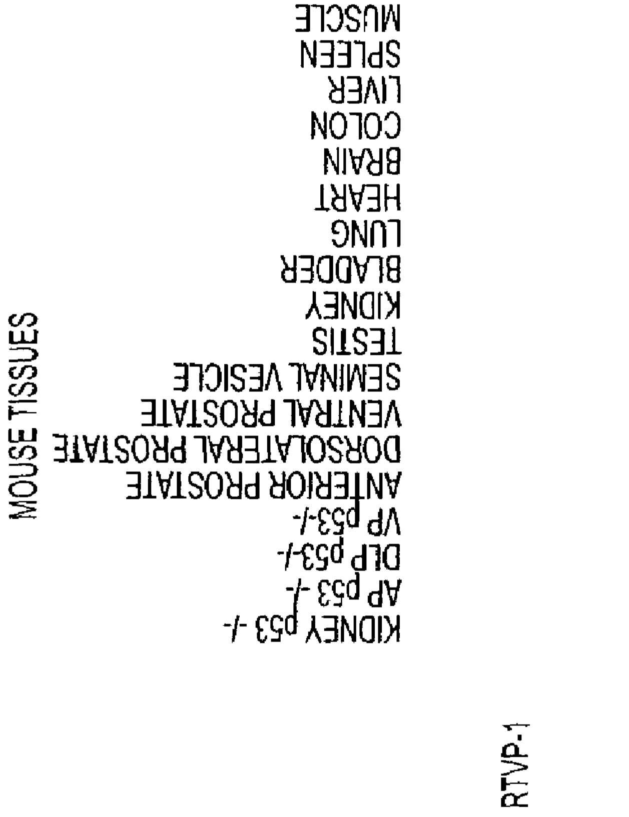
Figure 10D:
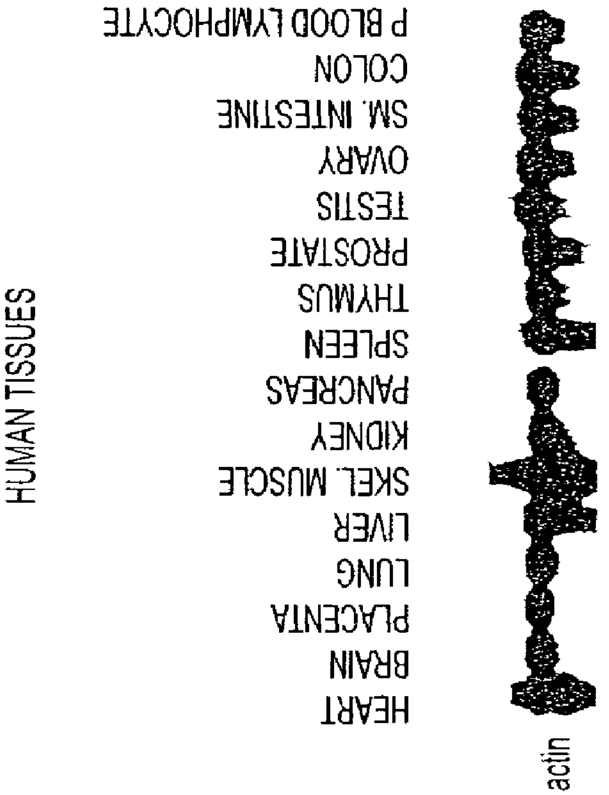
Figure 10B:
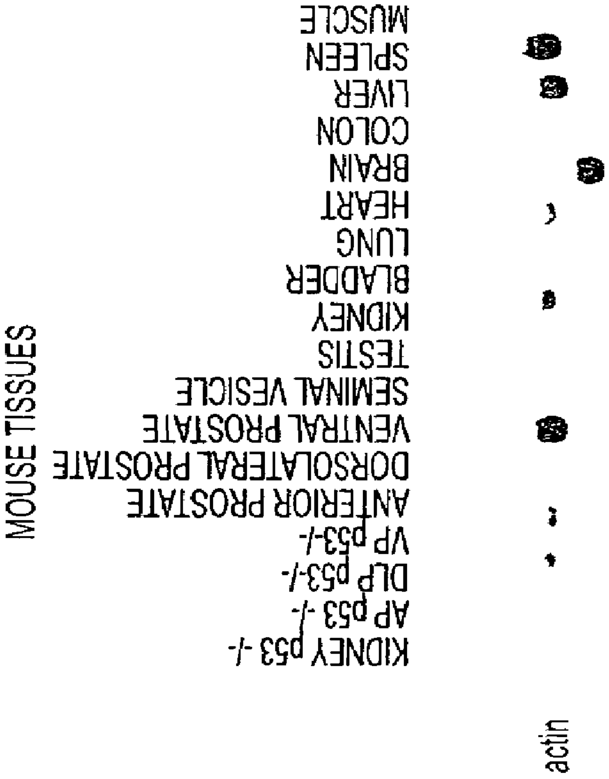
Figure 11:
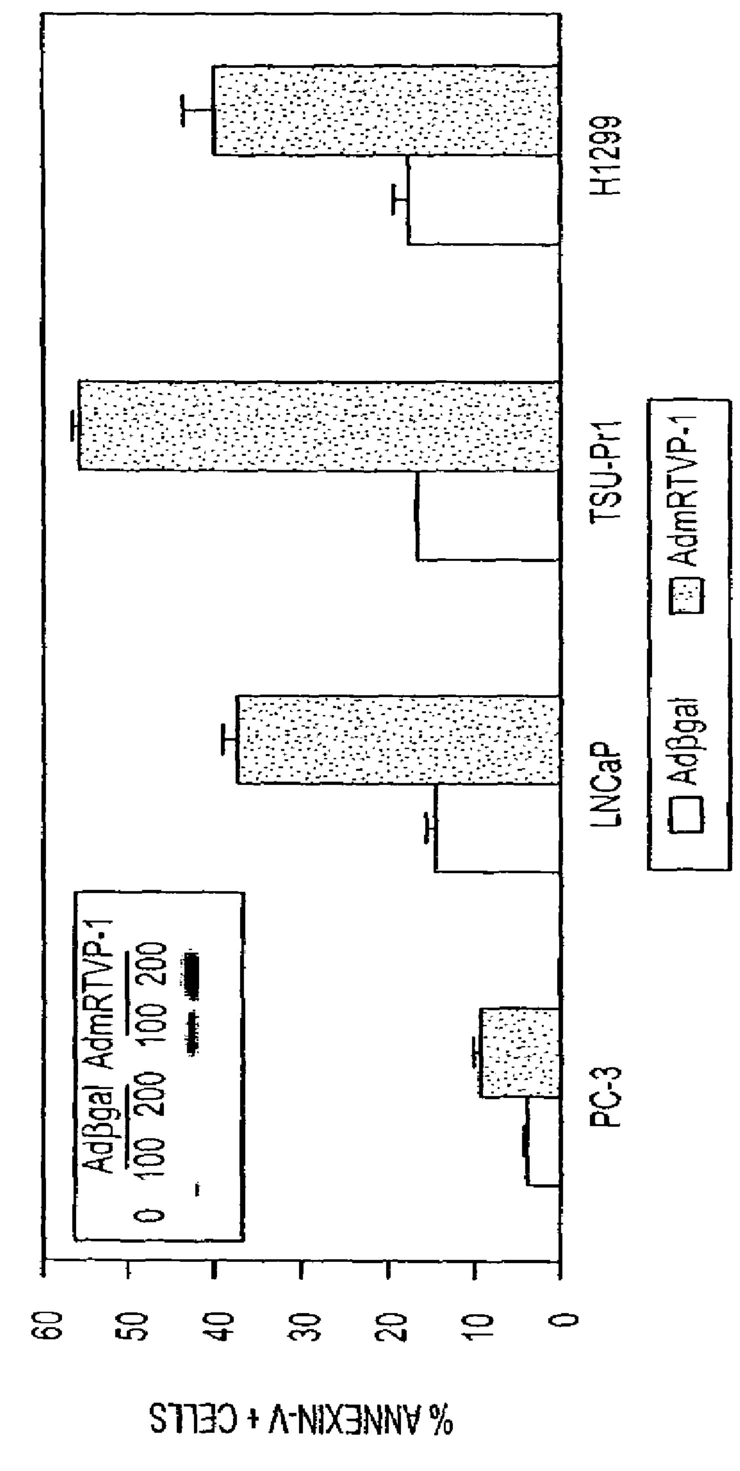
FIG. 11 Induction of apoptosis by mRTVP-1.
Figure 12A:
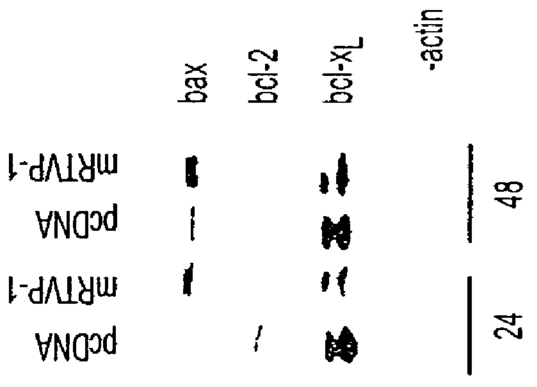
FIGS. 12A-12C Activation of mitochondrial pathways by mRTVP-1.
Figure 12B:
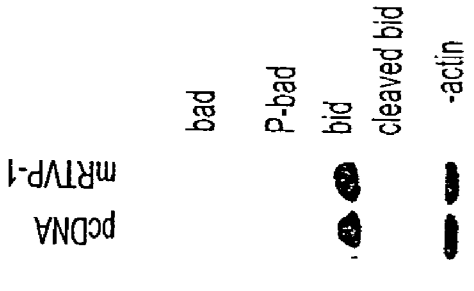
Figure 12C:
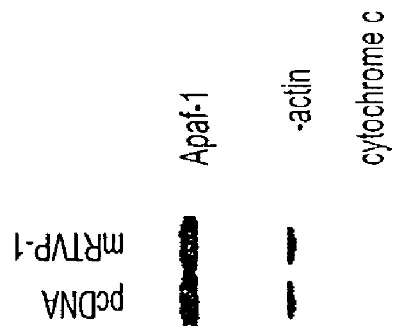
Figure 13:
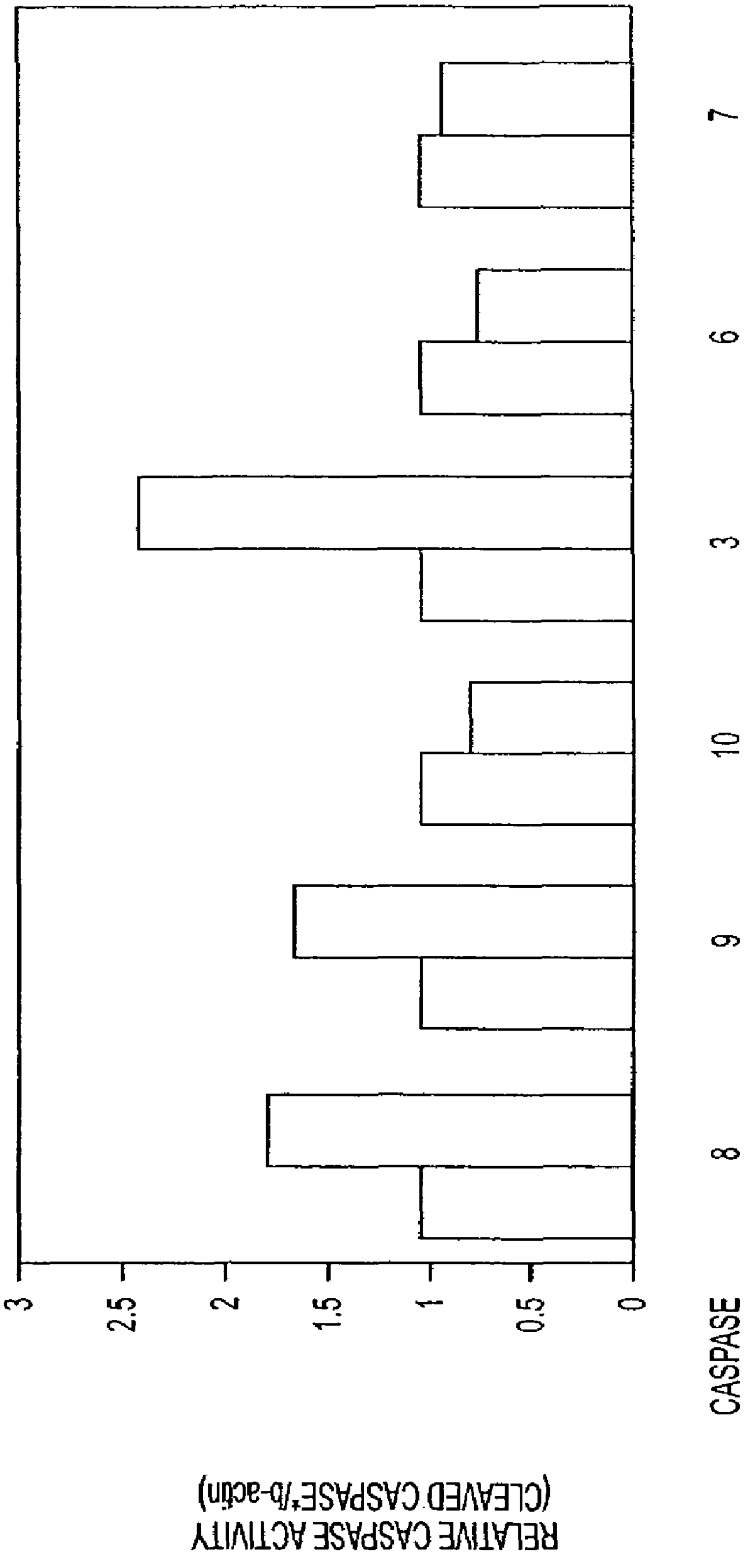
FIG. 13 Caspase activation by mRTVP-1.

To further explore the underlying mechanisms responsible for mRTVP-1 mediated anti-neoplastic activity, additional experiments were conducted. All experiments were performed as indicated or according to procedures which are well known to those of ordinary skill in the art. As shown in FIG. 7, p53 has an important role in the progression of prostate cancer (FIG. 7*a*), both for a bystander effect (FIG. 7*b*), and for regulation of genes in prostate cancer (FIG. 7*c*). Promoter constructs of both mutant and wild-type p53 demonstrate that regulation of the mRTVP-1 promoter require p53 binding (FIG. 8). Further, induction of mRTVP-1 was shown in both RM9 and TSU-Pr-1 cells by Adp53 by gamma irradiation (FIG. 9). RTVP-1 expression was evaluated for both mouse and human tissues (FIG. 10). Induction of apoptosis was shown in PC-3 cells, LNCaP cells, TSU-Prl cells and H1299 cells (FIG. 11), as well as activation of mitochondrial pathways by mRTVP-1 (FIG. 12), and caspase activation (FIG. 13).

Figure 14:
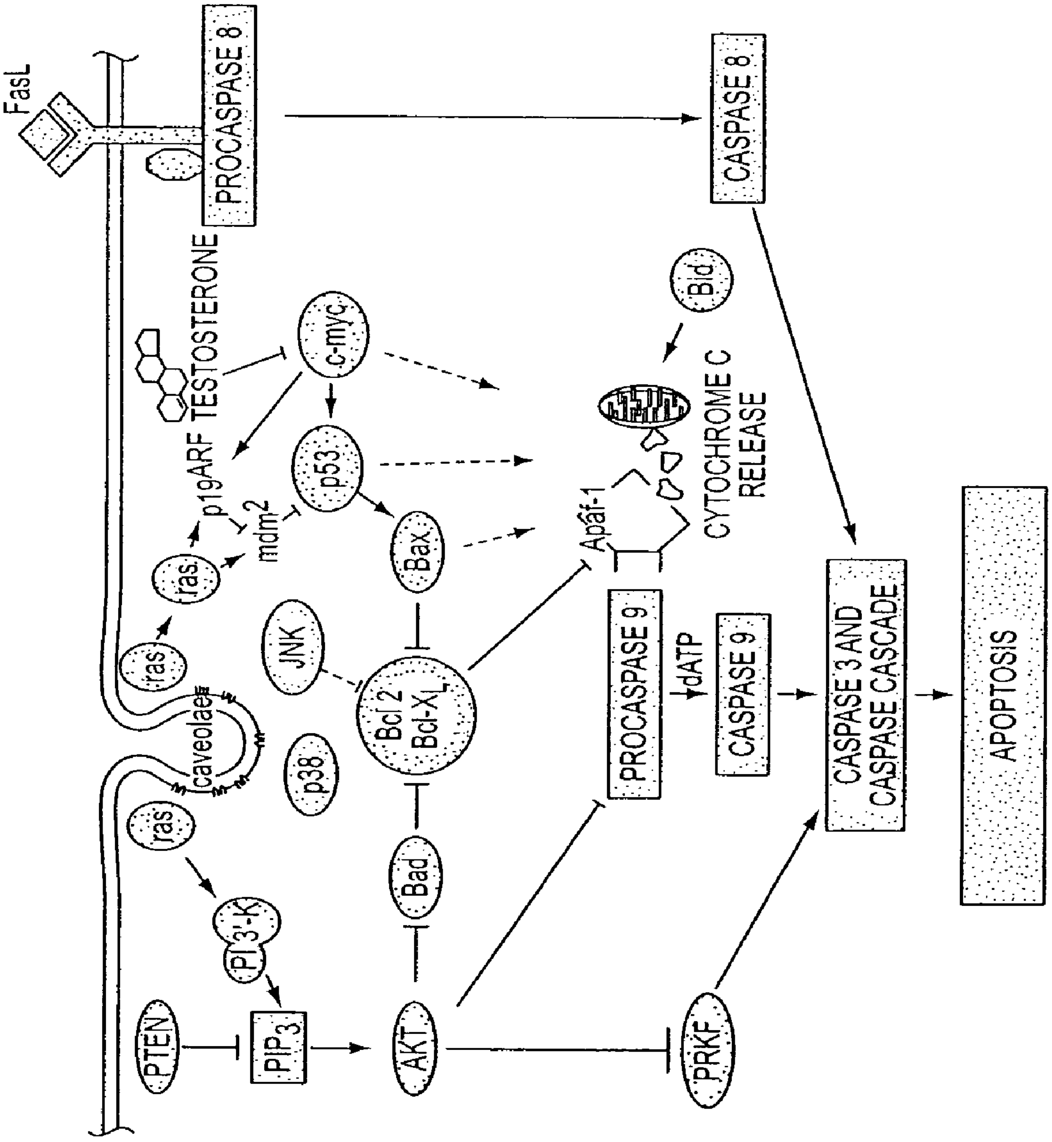
FIG. 14 Regulation of apoptosis in prostate cancer.
Figures 15A, 15B, 15C, 15D, 15E:
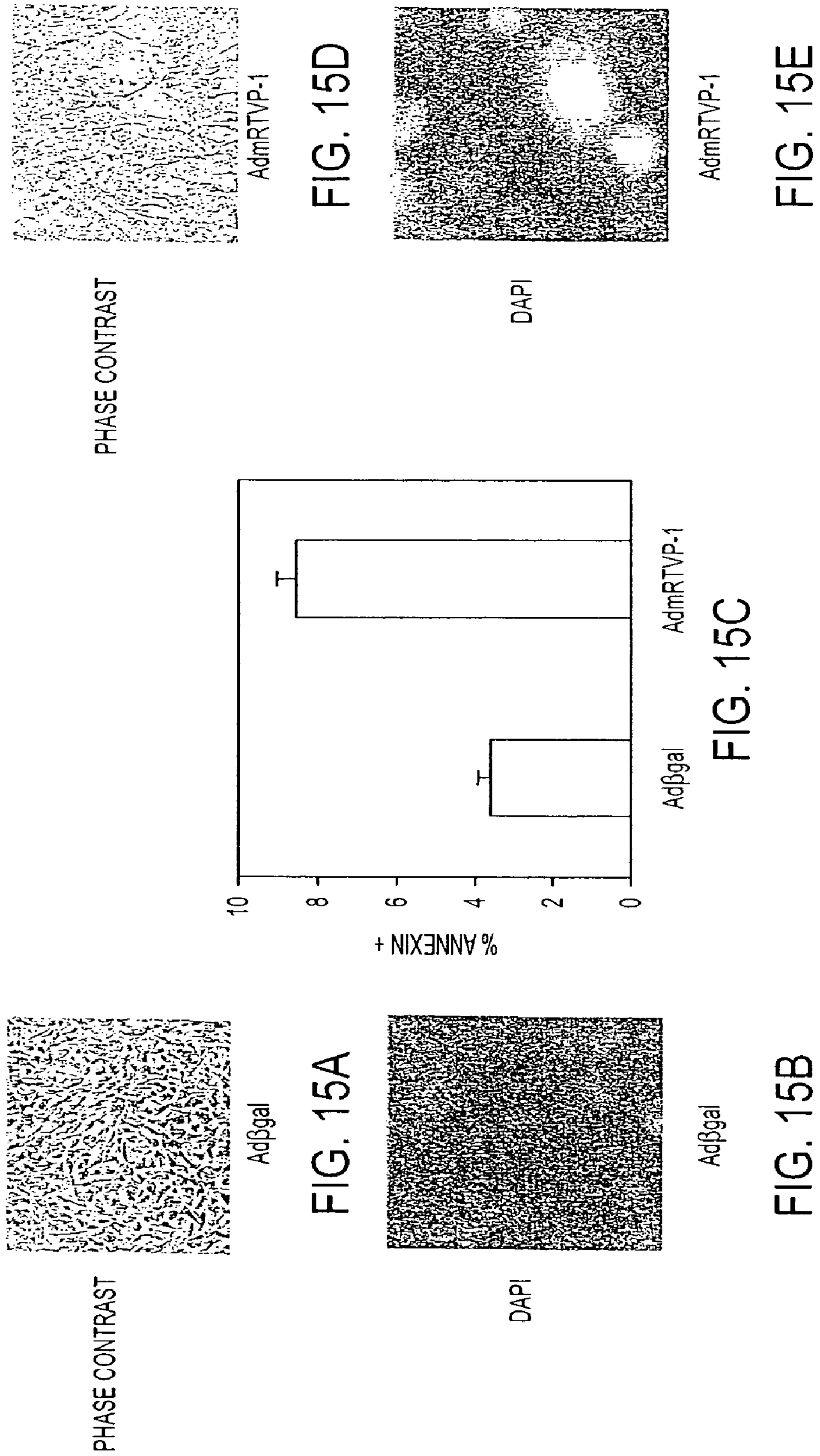
FIGS. 15A-15E Induction of apoptosis and morphological changes by AdmRTVP-1.
Figure 16:
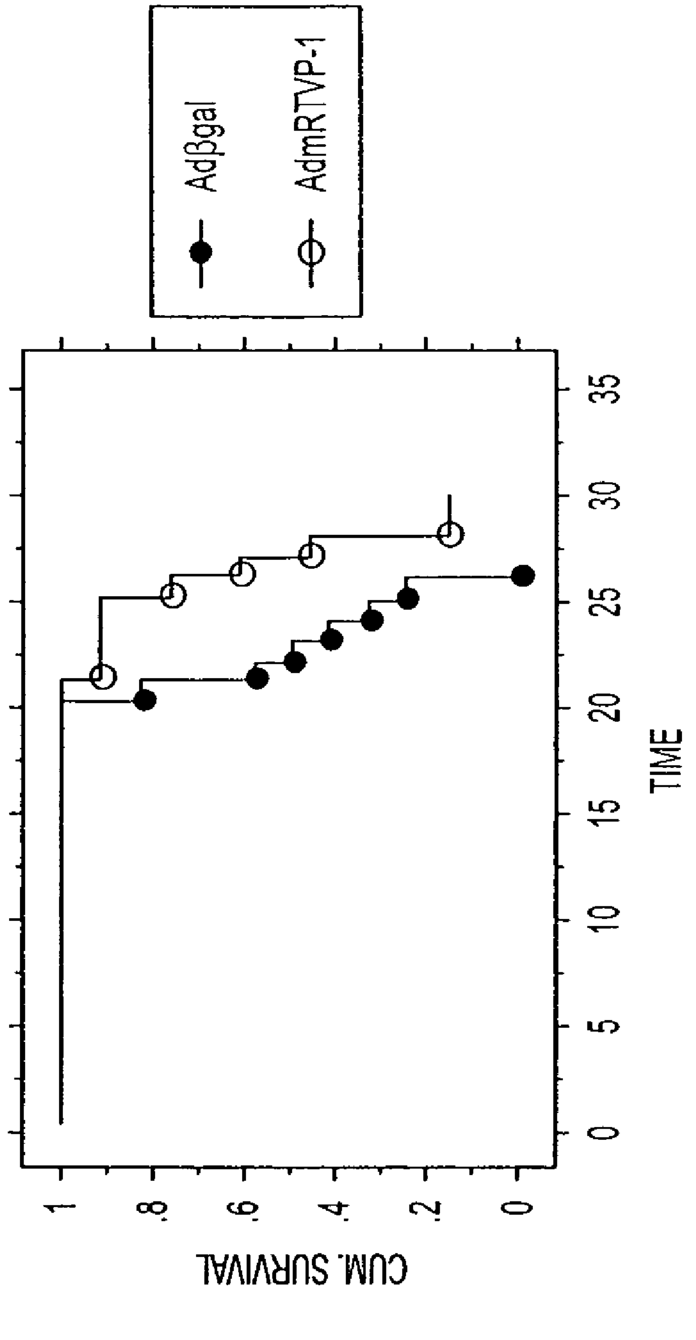
FIG. 16 Increased survival of mice with orthotopic tumors after AdmRTVP-1 treatment.
Figure 17:
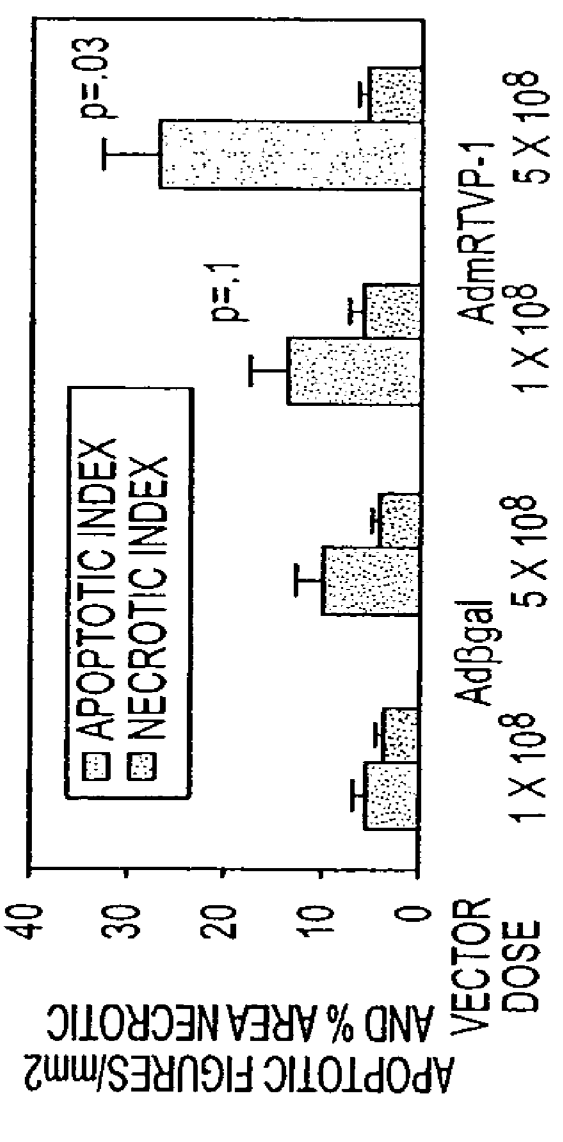
FIG. 17 Apoptosis in 178-2BMA orthotopic tumors.
Figures 1, 18A:
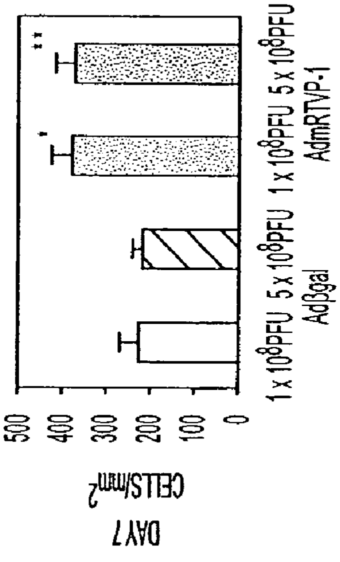
Figures 2, 18A:
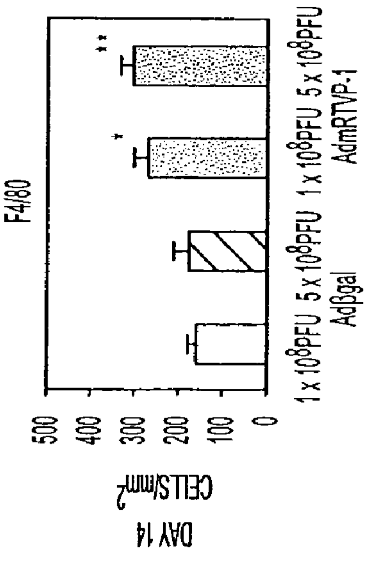
Figures 3, 18A:
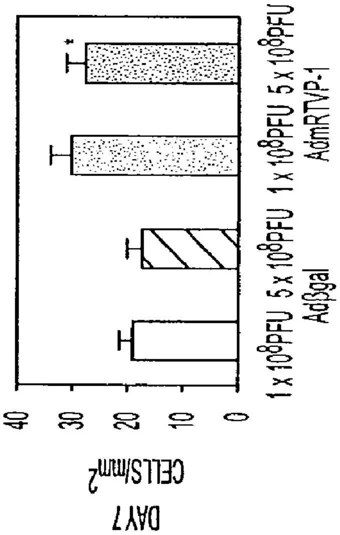
Figures 4, 18A:
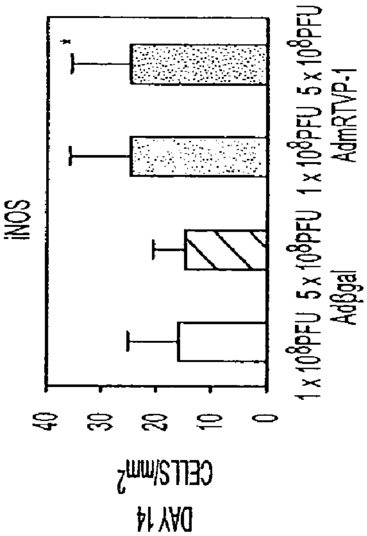
Figures 5, 18A:
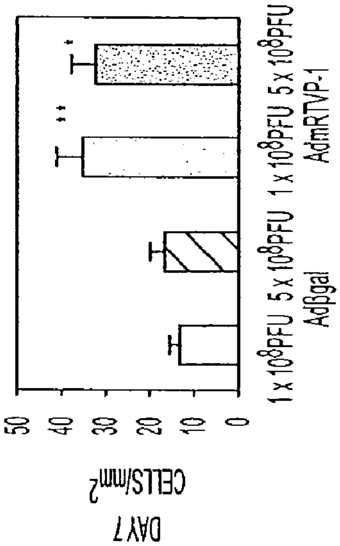
Figures 6, 18A:
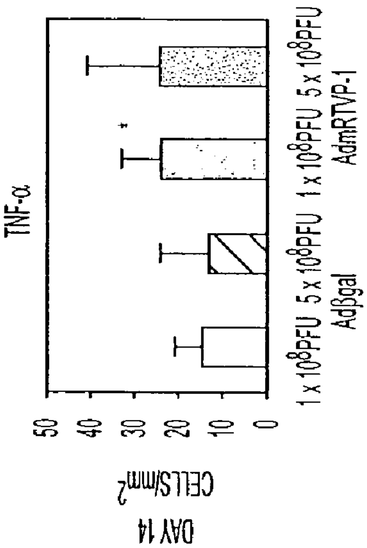
Figures 7, 18A:
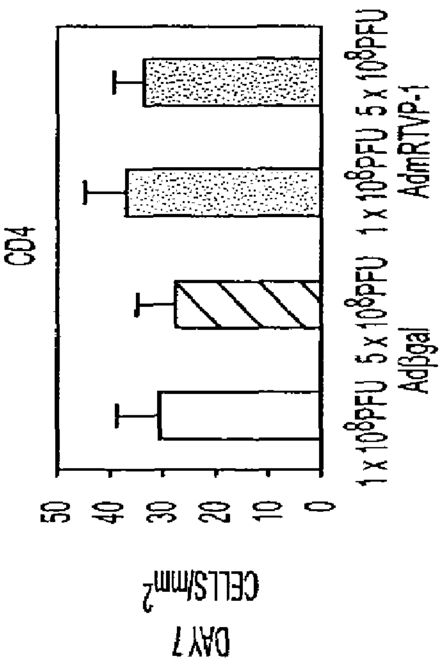
Figures 8, 18A:
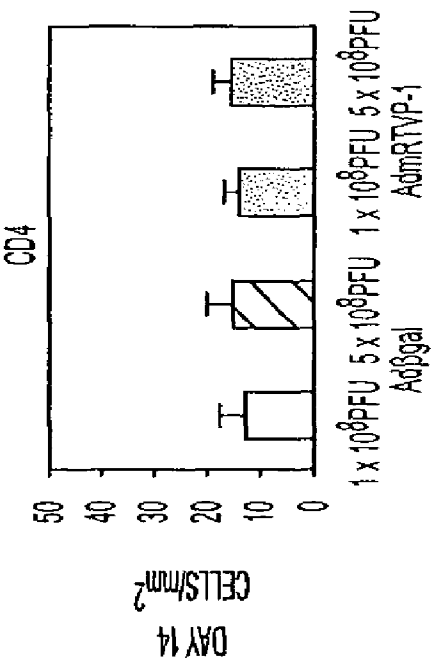
Figures 9, 18A:
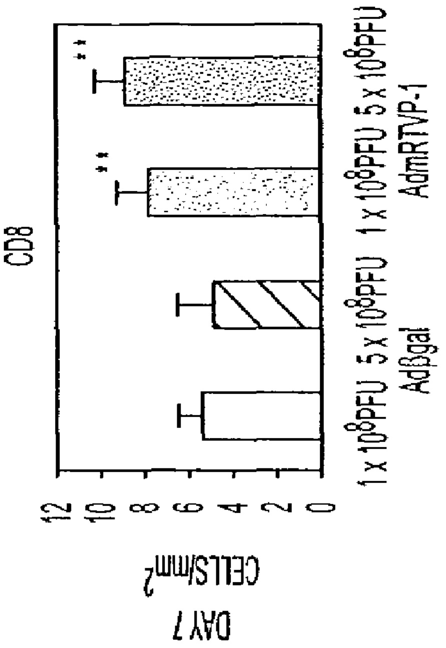
Figures 10, 18A:
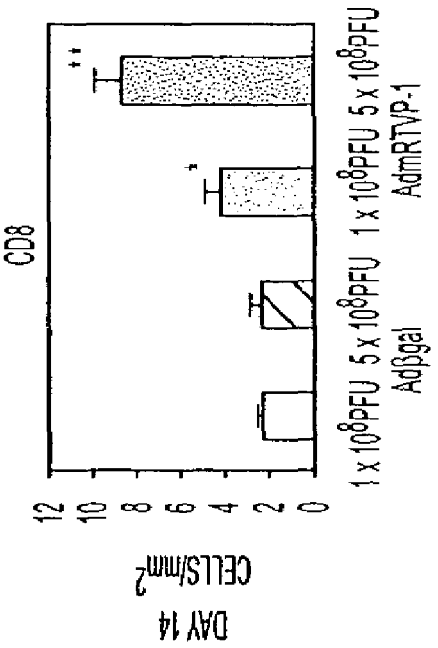
Figures 1, 18B:
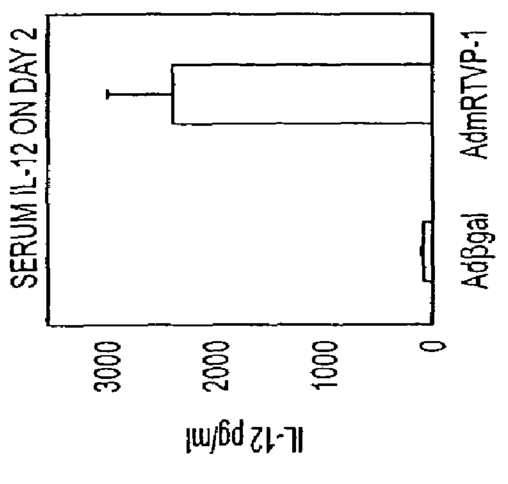
Figures 2, 18B:
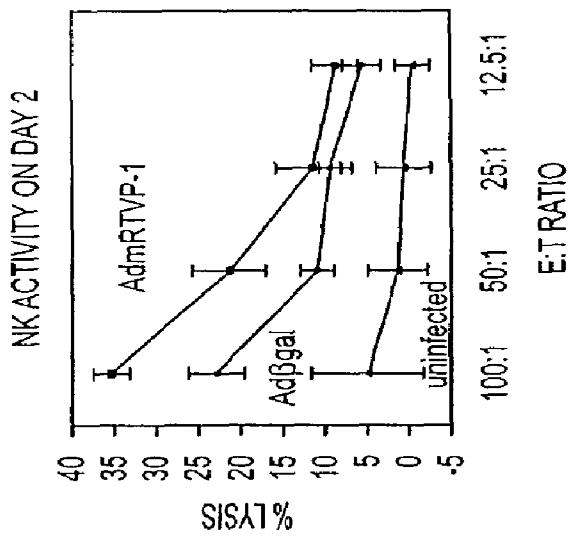
Figures 3, 18B:
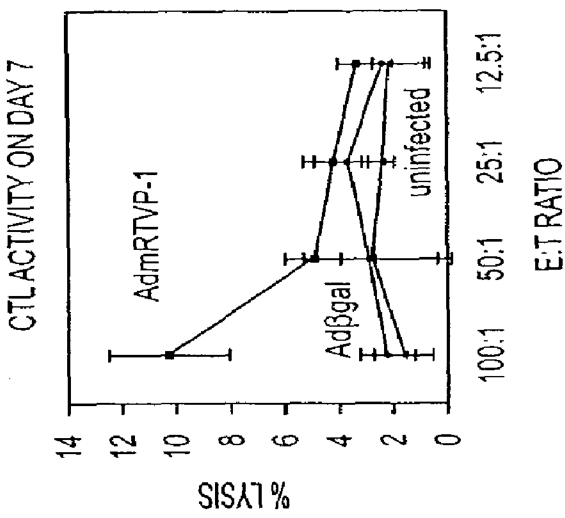
Figure 19B:
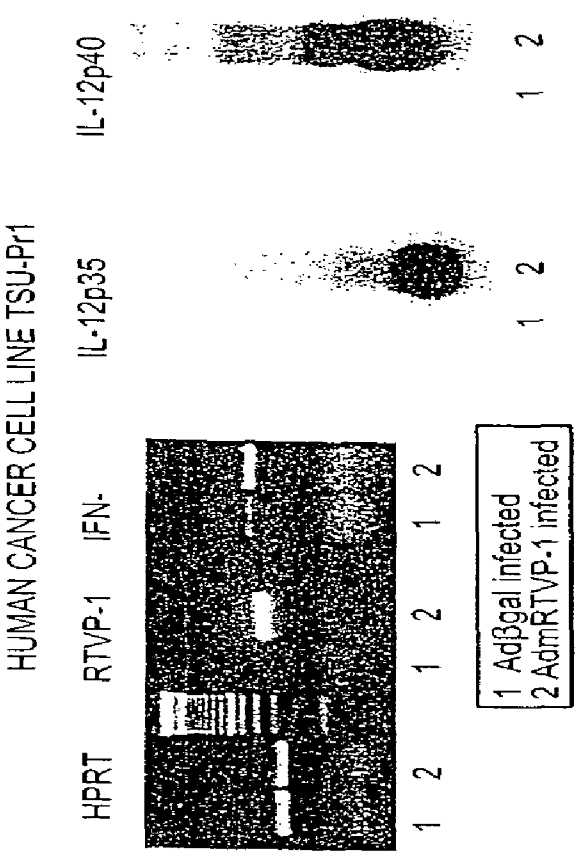
FIGS. 19A-19B Cytokine induction by mRTVP-1.
Figure 19A:
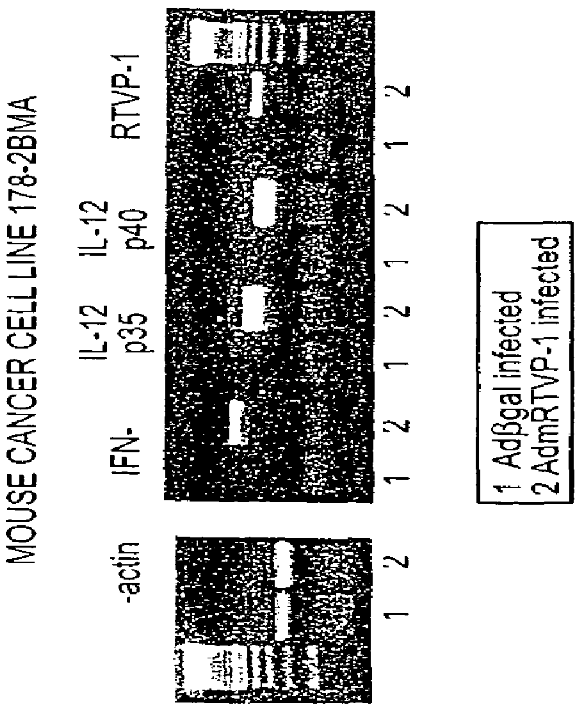
Figure 20B:
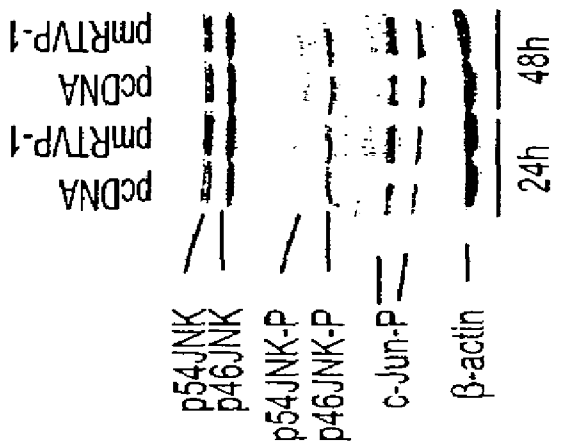
FIGS. 20A-20B Activation of JNK pathway by mRTVP-1.
Figure 20A:
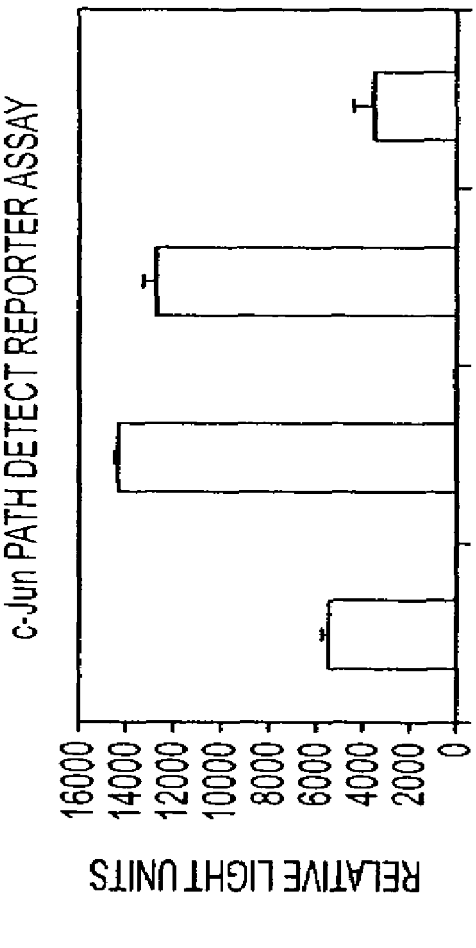
Figure 21:
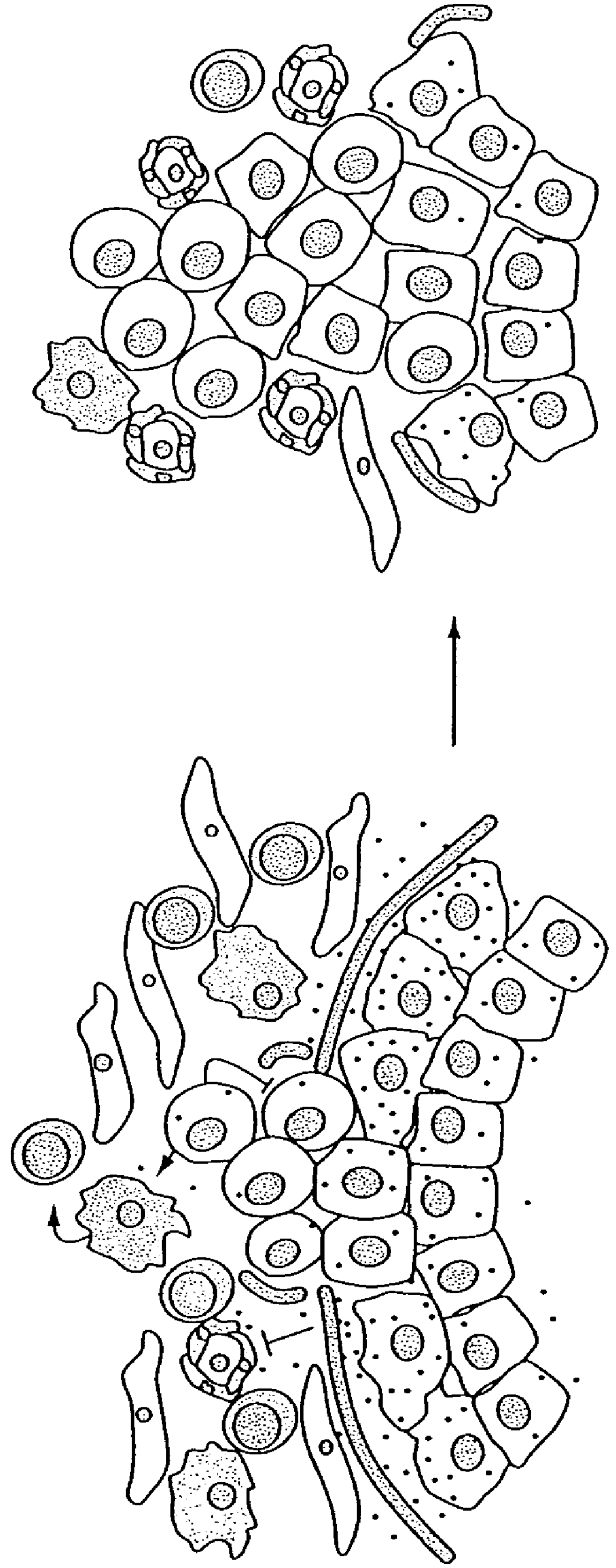
FIG. 21 Schematic showing potential mechanisms of mRTVP-1-mediated suppression of metastasis.
Figure 22:
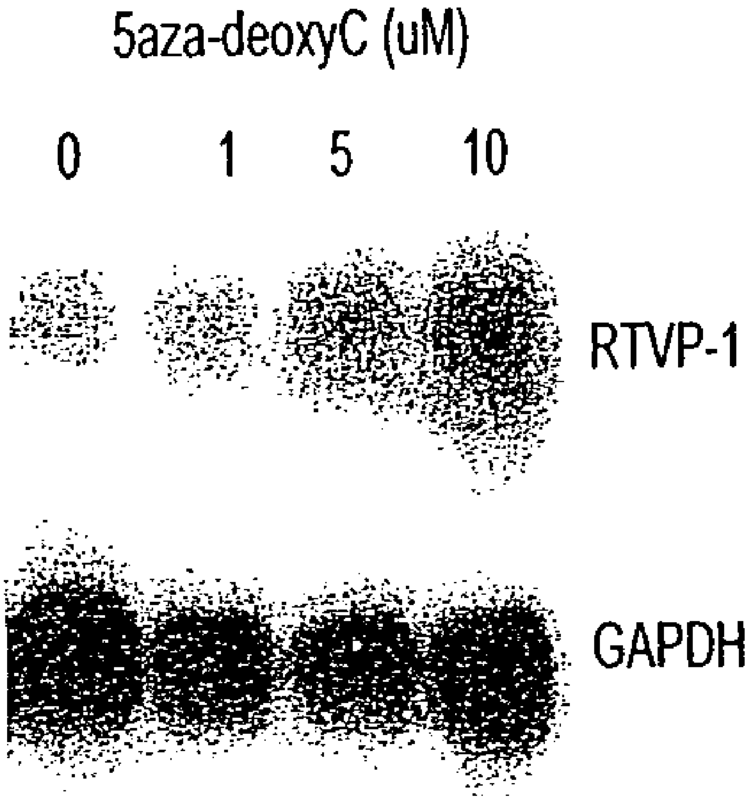
FIG. 22 Demethylation of 148-1PA cells induces RTVP-1 expression.

Experiments were also performed demonstrating a role for RTVP-1 in apoptosis of prostate cancer. A schematic is shown in FIG. 14, and the induction of apoptosis in 178-2BMA cells by AdmRTVP-1 in FIG. 15. Mice with orthotopic 178-2BMA tumor tissue treated with AdmRTVP-1 showed increased survival (FIG. 16), as well as necrosis of the tumor tissues (FIG. 17). Immune cell infiltrates were seen (FIG. 18*a*) and an immune response for IL-12, NK activity and CTL activity (FIG. 18*b*). Cytokine induction was shown for both mouse and human prostate cancer in vitro (FIG. 19), and mRTVP-1 was shown to activate the JNK signal transduction pathway (FIG. 20). Potential mechanisms of mRTVP-1-mediated suppression of metastasis are shown in FIG. 21. Demethylation of 148-1PA cells with increasing amounts of 5aza-deoxyC was shown to induce RTVP-1 (FIG. 22).

Other embodiments and uses of the invention will be apparent to those skilled in the art from consideration of the specification and practice of the invention disclosed herein. All references cited herein, including all publications, U.S. and foreign patents and patent applications including U.S. provisional application No. 60/209,989 entitled "P53 Regulated Gene Encoding p144-3 and p144-3 Protein," filed Jun. 8, 2000, are specifically and entirely hereby incorporated herein by reference. It is intended that the specification and examples be considered exemplary only, with the true scope and spirit of the invention indicated by the following claims.

TABLE 1

Homology Comparison to Mouse RTVP-1 (p144-3 clone)

| | Percent Match |
|---|---|
| *H. sapiens* mRNA for RTVP protein | 53.7 |
| Human glioma pathogenesis-related protein | 60.5 |
| *H. sapiens* mRNA for cysteine-rich secretory protein | 49.6 |
| *H. sapiens* mRNA for cysteine-rich secretory protein | 49.7 |
| *H. sapiens* mRNA for cysteine-rich secretory protein | 47.5 |
| Acidic epididymal glycoprotein gene | 49.3 |
| Human mRNA for acidic epididymal glycoprotein | 49.3 |
| Galago crassicaudatus encoding von Willebrand factor | 35.2 |
| Rat alpha2 urinary globulin gene | 23.5 |
| Human P450c21B gene coding for steroid | 34.6 |
| Human testes-specific protein (Tpx-1) | 47.1 |
| Mouse surfeit locus surfeit 3 gene | 35.3 |

TABLE 2

RTVP-1 mRNA expression in human prostate specimens by in situ hybridization

| | RTVP-1 mRNA score† | % (n) | P53 staining‡ in RTVP-1 positive specimens % (n) |
|---|---|---|---|
| Normal glandular cells | | | |
| | + | 0 (0/5) | |
| | ++ | 40 (2/5) | |
| | +++ | 60 (3/5) | |
| Primary cancer cells | | | |
| | + | 12 (2/16) | 50 (1/2) |
| | +++ | 69 (11/16) | 36 (4/11) |
| | +++ | 19 (3/16) | 0 (0/3) |
| Lymph node metastatic cancer cells* | | | |
| | + | 60 (3/5) | 67 (2/3) |
| | ++ | 40 (2/5) | 0 (0/2) |
| | +++ | 0 (0/5) | |

†RTVP-1 mRNA in cells scored as: – no signal detected; + low; ++ moderate; or +++ high level of fluorescence intensity.
‡Presence or absence of clustered p53 staining (>15 cancer cell nuclei p53 +/ 300 × 400 $\mu m^2$ field)
*(P=.036, Mann-Whitney U test RTVP-1 mRNA score for lymph node metastatic cancer cells compared to primary cancer cells).

REFERENCES 1. el-Deiry, W. S. Regulation of p53 downstream genes. *Semin Cancer Biol* 8, 345-57 (1998).
2. Giaccia, A. J. & Kastan, M. B. The complexity of p53 modulation: emerging patterns from divergent signals. *Genes Dev* 12, 2973-83 (1998).
3. Burns, T. F. & El-Deiry, W. S. The p53 pathway and apoptosis. *J Cell Physiol* 181, 231-9 (1999).
4. Vogelstein, B. & Kinzler, K. W. p53 function and dysfunction. *Cell* 70, 523-6 (1992).
5. Thompson, T. C., Timme, T. L. & Sehgal, I. Oncogenes, growth factors, and hormones in prostate cancer in *Hormones and growth factors in development and neoplasia*. (eds. Dickson, R. B. & Salomon, D. S.) 327-359 (Wiley-Liss, Inc., New York, 1998).
6. Thompson, T. C. et al. Loss of p53 function leads to metastasis in ras+myc-initiated mouse prostate cancer. *Oncogene* 10, 869-79 (1995).
7. Navone, N. M. et al. p53 protein accumulation and gene mutation in the progression of human prostate carcinoma. *J Natl Cancer Inst* 85, 1657-69 (1993).
8. Eastham, J. A. et al. Association of p53 mutations with metastatic prostate cancer. *Clin Cancer Res* 1, 1111-8 (1995).
9. Mirchandani, D. et al. Heterogeneity in intratumor distribution of p53 mutations in human prostate cancer. *Am J Pathol* 147, 92-101 (1995).
10. Yang, G. et al. Clustered p53 immunostaining: a novel pattern associated with prostate cancer progression. *Clin Cancer Res* 2, 399-401 (1996).
11. Stapleton, A. M. et al. Primary human prostate cancer cells harboring p53 mutations are clonally expanded in metastases. *Clin Cancer Res* 3, 1389-97 (1997).
12. Quinn, D. I. et al. Prognostic significance of p53 nuclear accumulation in localized prostate cancer treated with radical prostatectomy. *Cancer Res* 60, 1585-94 (2000).
13. Stapleton, A. M. et al. Assessment of the biologic markers p53, Ki-67, and apoptotic index as predictive indicators of prostate carcinoma recurrence after surgery. *Cancer* 82, 168-75 (1998).
14. Miyashita, T. & Reed, J. C. Tumor suppressor p53 is a direct transcriptional activator of the human bax gene. *Cell* 80, 293-9. (1995).
15. Sheikh, M. S. et al. p53-dependent and -independent regulation of the death receptor KILLER/DR5 gene expression in response to genotoxic stress and tumor necrosis factor alpha. *Cancer Res* 58, 1593-8 (1998). 16. Oda, K. et al. p53AIP1, a potential mediator of p53-dependent apoptosis, and its regulation by Ser-46-phosphorylated p53. *Cell* 102, 849-62 (2000).
17. Zhu, J. & Chen, X. MCG10, a novel p53 target gene that encodes a KH domain RNA-binding protein, is capable of inducing apoptosis and cell cycle arrest in G(2)-M. *Mol Cell Biol* 20, 5602-18 (2000).
18. Dameron, K. M., Volpert, O. V., Tainsky, M. A. & Bouck, N. Control of angiogenesis in fibroblasts by p53 regulation of thrombospondin-1. *Science* 265, 1582-4 (1994).
19. Lopez-Ocejo, O. et al. Oncogenes and tumor angiogenesis: the HPV-16 E6 oncoprotein activates the vascular endothelial growth factor (VEGF) gene promoter in a p53 independent manner. *Oncogene* 19, 4611-20 (2000).
20. Zou, Z. et al. p53 regulates the expression of the tumor suppressor gene maspin. *J Biol Chem* 275, 6051-4 (2000).
21. Zhang, M., Volpert, O., Shi, Y. H. & Bouck, N. Maspin is an angiogenesis inhibitor. *Nat Med* 6, 196-9 (2000).

22. Zhang, Y., Griffith, E. C., Sage, J., Jacks, T. & Liu, J. O. Cell cycle inhibition by the anti-angiogenic agent TNP-470 is mediated by p53 and p21WAF1/CIP1. *Proc Natl Acad Sci USA* 97, 6427-32 (2000).

23. Murphy, E. V., Zhang, Y., Zhu, W. & Biggs, J. The human glioma pathogenesis-related protein is structurally related to plant pathogenesis-related proteins and its gene is expressed specifically in brain tumors. *Gene* 159, 131-5. (1995).

24. Rich, T., Chen, P., Furman, F., Huynh, N. & Israel, M. A. RTVP-1, a novel human gene with sequence similarity to genes of diverse species, is expressed in tumor cell lines of glial but not neuronal origin. *Gene* 180, 125-30 (1996).

25. Gingras, M. C. & Margolin, J. F. Differential expression of multiple unexpected genes during U937 cell and macrophage differentiation detected by suppressive subtractive hybridization. *Exp Hematol* 28, 65-76 (2000).

26. Cho, Y., Gorina, S., Jeffrey, P. D. & Pavletich, N. P. Crystal structure of a p53 tumor suppressor-DNA complex: understanding tumorigenic mutations. *Science* 265, 346-55 (1994).

27. Tokino, T. et al. p53 tagged sites from human genomic DNA. Hum Mol Genet 3, 1537-42 (1994).

28. Yu, J. et al. Identification and classification of p53-regulated genes. *Proc Natl Acad Sci USA* 96, 14517-22 (1999).

29. Shiraishi, K. et al. Identification of fractalkine, a CX3C-type chemokine, as a direct target of p53. *Cancer Res* 60, 3722-6 (2000).

30. Bazan, J. F. et al. A new class of membrane-bound chemokine with a CX3C motif. *Nature* 385, 640-4. (1997).

31. Pan, Y. et al. Neurotactin, a membrane-anchored chemokine upregulated in brain inflammation. *Nature* 387, 611-7. (1997).

32. Sakr, W. A. et al. Allelic loss in locally metastatic, multisampled prostate cancer. *Cancer Res* 54, 3273-7 (1994).

33. Qian, J. et al. Chromosomal anomalies in prostatic intraepithelial neoplasia and carcinoma detected by fluorescence in situ hybridization. *Cancer Res* 55, 5408-14 (1995).

34. Ren, C., Yang, G., Timme, T. L., Wheeler, T. M. & Thompson, T. C. Reduced lysyl oxidase messenger RNA levels in experimental and human prostate cancer. *Cancer Res* 58, 1285-90 (1998).

35. Yang, G. et al. Elevated expression of caveolin is associated with prostate and breast cancer. *Clin Cancer Res* 4, 1873-80 (1998).

36. Nasu, Y. et al. Suppression of caveolin expression induces androgen sensitivity in metastatic androgen-insensitive mouse prostate cancer cells. *Nat Med* 4, 1062-4 (1998).

37. Baker, S. J., Markowitz, S., Fearon, E. R., Willson, J. K. & Vogelstein, B. Suppression of human colorectal carcinoma cell growth by wild-type p53. *Science* 249, 912-5. (1990).

38. Timme, T. L. et al. Caveolin-1 is regulated by c-myc and suppresses c-myc-induced apoptosis. *Oncogene* 19, 3256-65 (2000).

39. Patel, S. D. et al. The p53-independent tumoricidal activity of an adenoviral vector encoding a p27-p16 fusion tumor suppressor gene. *Mol Ther* 2, 161-9. (2000).

40. Hall, S. J. et al. Cooperative therapeutic effects of androgen ablation and adenovirus-mediated herpes simplex virus thymidine kinase gene and ganciclovir therapy in experimental prostate cancer. *Cancer Gene Ther* 6, 54-63 (1999).

41. Nasu, Y. et al. Adenovirus-mediated interleukin-12 gene therapy for prostate cancer: suppression of orthotopic tumor growth and pre-established lung metastases in an orthotopic model. *Gene Ther* 6, 338-49 (1999).

42. Eastham, J. A. et al. In vivo gene therapy with p53 or p21 adenovirus for prostate cancer. *Cancer Res* 55, 5151-5. (1995).

43. Baley, P. A., Yoshida, K., Qian, W., Sehgal, I. & Thompson, T. C. Progression to androgen insensitivity in a novel in vitro mouse model for prostate cancer. *J Steroid Biochem Mol Biol* 52, 403-13 (1995).

44. Osoegawa, K. et al. Bacterial artificial chromosome libraries for mouse sequencing and functional analysis. *Genome Res* 10, 116-28. (2000).

The invention claimed is:

1. A method for treating prostate cancer in a patient comprising administering to the patient a therapeutically effective amount of a composition comprising the amino acid sequence of SEQ ID NO:3, wherein said composition has anti-neoplastic activity, and wherein the cancer exhibits reduced expression of RTVP-1 relative to histologically normal prostate tissue.

2. The method of claim 1 wherein the anti-neoplastic activity is selected from the group consisting of modulation of an immune response, induction of apoptosis, anti-angiogenic activity and combinations thereof

3. The method of claim 1 wherein the patient is a human.

4. The method of claim 1 wherein said composition induces apoptosis in human prostate cancer cells.

* * * * *

SEQUENCE LISTING

```
<160> NUMBER OF SEQ ID NOS: 5

<210> SEQ ID NO 1
<211> LENGTH: 1008
<212> TYPE: DNA
<213> ORGANISM: Mus sp.

<400> SEQUENCE: 1

tggagctcag aggcagagca cttgtctagc ataaacaacc ctgggttaat ccgagctcca      60

acagggaaac agtctgcaga ctgagagaac cgagcattct atcagaaccc cgcagctctg     120

gattctaggt ccagcagcaa ccagagagac catgcaggtc atccttgctg tgatagtctg     180

gatggcttcg tctgtgtcta gttcttcatt tacagcaagc actttgccag atataacaaa     240

cgaggacttc attaaagaat gtgttcaagt tcacaaccag cttcggtcaa aagtgagtcc     300

accagcccgg aatatgctgt acatgtcttg ggacccaaaa ctagcccaaa ttgcaaaagc     360

atggacaaaa tcttgtgaat ttaaacacaa cccacagctg cattcacgga tacacccaaa     420

tttcaccgcc ctgggagaga atatctggct tggctctcta tccatctttt cagtatcctc     480

agccatctct gcctggtatg aagaaattaa gcactatgac ttcagcacta ggaaatgtag     540

acatgtctgt ggccattata ctcaggttgt ttgggcagac agttacaaac ttggctgtgc     600
```

-continued

```
agtgcaactt tgccctaatg gagcaaattt tatatgcgac tatggaccag caggaaatta    660

cccaacgtgg ccatataagc aaggagccac gtgcagtgat tgcccaaaag atgacaagtg    720

tctcaacagt ctctgattaa cccacgacga gaccaggtct cacgttacta ctctgtcgca    780

ttatccagac tggcctatat acctgcgtaa cagatacaca tctctctttc tcattgctaa    840

gtcggttctc ctattactgt ctgttataat taccatctgg gtaaagcaca aatatcctaa    900

cttggttctt ttggactaaa gctgtggttg ggggacaact gaatcacatg cggctattta    960

aaaacttttc aataaaatct cagtcaaaag aaaaaaaaaa aaaaaaaa                1008


<210> SEQ ID NO 2
<211> LENGTH: 255
<212> TYPE: PRT
<213> ORGANISM: Mus sp.

<400> SEQUENCE: 2

Met Gln Val Ile Leu Ala Val Ile Val Trp Met Ala Ser Ser Val Ser
1               5                   10                  15

Ser Ser Ser Phe Thr Ala Ser Thr Leu Pro Asp Ile Thr Asn Glu Asp
            20                  25                  30

Phe Ile Lys Glu Cys Val Gln Val His Asn Gln Leu Arg Ser Lys Val
        35                  40                  45

Ser Pro Pro Ala Arg Asn Met Leu Tyr Met Ser Trp Asp Pro Lys Leu
    50                  55                  60

Ala Gln Ile Ala Lys Ala Trp Thr Lys Ser Cys Glu Phe Lys His Asn
65                  70                  75                  80

Pro Gln Leu His Ser Arg Ile His Pro Asn Phe Thr Ala Leu Gly Glu
                85                  90                  95

Asn Ile Trp Leu Gly Ser Leu Ser Ile Phe Ser Val Ser Ser Ala Ile
            100                 105                 110

Ser Ala Trp Tyr Glu Glu Ile Lys His Tyr Asp Phe Ser Thr Arg Lys
        115                 120                 125

Cys Arg His Val Cys Gly His Tyr Thr Gln Val Val Trp Ala Asp Ser
    130                 135                 140

Tyr Lys Leu Gly Cys Ala Val Gln Leu Cys Pro Asn Gly Ala Asn Phe
145                 150                 155                 160

Ile Cys Asp Tyr Gly Pro Ala Gly Asn Tyr Pro Thr Trp Pro Tyr Lys
                165                 170                 175

Gln Gly Ala Thr Cys Ser Asp Cys Pro Lys Asp Asp Lys Cys Leu Asn
            180                 185                 190

Ser Leu Cys Ile Asn Pro Arg Arg Asp Gln Val Ser Arg Tyr Tyr Ser
        195                 200                 205

Val Asp Tyr Pro Asp Trp Pro Ile Tyr Leu Arg Asn Arg Tyr Thr Ser
    210                 215                 220

Leu Phe Leu Ile Ala Lys Ser Val Leu Leu Leu Leu Ser Val Ile Ile
225                 230                 235                 240

Thr Ile Trp Val Lys His Lys Tyr Pro Asn Leu Val Leu Leu Asp
                245                 250                 255


<210> SEQ ID NO 3
<211> LENGTH: 266
<212> TYPE: PRT
<213> ORGANISM: Homo sapiens

<400> SEQUENCE: 3

Met Arg Val Thr Leu Ala Thr Ile Ala Trp Met Val Ser Phe Val Ser
```

-continued

```
1               5                   10                  15

Asn Tyr Ser His Thr Ala Asn Ile Leu Pro Asp Ile Glu Asn Glu Asp
            20                  25                  30

Phe Ile Lys Asp Cys Val Arg Ile His Asn Lys Phe Arg Ser Glu Val
        35                  40                  45

Lys Pro Thr Ala Ser Asp Met Leu Tyr Met Ile Trp Asp Pro Ala Leu
    50                  55                  60

Ala Gln Ile Ala Lys Ala Trp Ala Ser Asn Cys Gln Phe Ser His Asn
65                  70                  75                  80

Thr Arg Leu Lys Pro Pro His Lys Ile His Pro Asn Phe Thr Ser Leu
                85                  90                  95

Gly Glu Asn Ile Trp Thr Gly Ser Val Pro Ile Phe Ser Val Ser Ser
            100                 105                 110

Ala Ile Thr Asn Trp Tyr Asp Glu Ile Gln Asp Tyr Asp Phe Lys Thr
        115                 120                 125

Arg Ile Cys Lys Lys Val Cys Gly His Tyr Thr Gln Val Val Trp Ala
    130                 135                 140

Asp Ser Tyr Lys Val Gly Cys Ala Val Gln Phe Cys Pro Lys Val Ser
145                 150                 155                 160

Gly Phe Asp Ala Leu Ser Asn Gly Ala His Phe Ile Cys Asn Tyr Gly
                165                 170                 175

Pro Gly Gly Asn Tyr Pro Thr Trp Pro Tyr Lys Arg Gly Ala Thr Cys
            180                 185                 190

Ser Ala Cys Pro Asn Asn Asp Lys Cys Leu Asp Asn Leu Cys Val Asn
        195                 200                 205

Arg Gln Arg Asp Gln Val Lys Arg Tyr Tyr Ser Val Val Tyr Pro Gly
    210                 215                 220

Trp Pro Ile Tyr Pro Arg Asn Arg Tyr Thr Ser Leu Phe Leu Ile Val
225                 230                 235                 240

Asn Ser Val Ile Leu Ile Leu Ser Val Ile Ile Thr Ile Leu Val Gln
                245                 250                 255

Leu Lys Tyr Pro Asn Leu Val Leu Leu Asp
            260                 265
```

<210> SEQ ID NO 4
<211> LENGTH: 21
<212> TYPE: PRT
<213> ORGANISM: Mus sp.
<220> FEATURE:
<221> NAME/KEY: MISC_FEATURE
<222> LOCATION: (11)..(11)
<223> OTHER INFORMATION: x=n which = 1-22 nucleotides

<400> SEQUENCE: 4

```
Arg Arg Arg Cys Trp Trp Gly Tyr Tyr Tyr Xaa Arg Arg Arg Cys Trp
1               5                   10                  15

Trp Gly Tyr Tyr Tyr
            20
```

<210> SEQ ID NO 5
<211> LENGTH: 9
<212> TYPE: PRT
<213> ORGANISM: Homo sapiens

<400> SEQUENCE: 5

```
Lys Val Ser Gly Phe Asp Ala Leu Ser
1               5
```